United States Patent
Vakkalanka et al.

(10) Patent No.: US 9,737,521 B2
(45) Date of Patent: Aug. 22, 2017

(54) PHARMACEUTICAL COMPOSITIONS CONTAINING A PDE4 INHIBITOR AND A PI3 DELTA OR DUAL PI3 DELTA-GAMMA KINASE INHIBITOR

(71) Applicant: Rhizen Pharmaceuticals SA, La Chaux-de-Fonds (CH)

(72) Inventors: Swaroop K. Vakkalanka, La Chaux-de-Fonds (CH); Srikant Viswanadha, Hyderabad (IN)

(73) Assignee: Rhizen Pharmaceuticals SA, La Chaux-de-Fonds (CH)

( * ) Notice: Subject to any disclaimer, the term of this patent is extended or adjusted under 35 U.S.C. 154(b) by 0 days.

(21) Appl. No.: 14/441,758

(22) PCT Filed: Nov. 7, 2013

(86) PCT No.: PCT/IB2013/059983
§ 371 (c)(1),
(2) Date: May 8, 2015

(87) PCT Pub. No.: WO2014/072937
PCT Pub. Date: May 15, 2014

(65) Prior Publication Data
US 2015/0272936 A1  Oct. 1, 2015

(30) Foreign Application Priority Data

Nov. 8, 2012 (IN) .......................... 2762/CHE/2012
Nov. 8, 2012 (IN) .......................... 4688/CHE/2012

(51) Int. Cl.
*A61K 31/44* (2006.01)
*A61K 45/06* (2006.01)
*A61K 31/52* (2006.01)
*A61K 31/519* (2006.01)

(52) U.S. Cl.
CPC ............ *A61K 31/44* (2013.01); *A61K 31/519* (2013.01); *A61K 31/52* (2013.01); *A61K 45/06* (2013.01)

(58) Field of Classification Search
CPC .......... A61K 31/44; A61K 31/52; A61K 45/06
See application file for complete search history.

(56) References Cited

U.S. PATENT DOCUMENTS 7,932,260 B2 * 4/2011 Fowler ................ C07D 473/16
514/266.1
8,642,607 B2 * 2/2014 Muthuppalaniappan C07D 311/36
514/262.1

FOREIGN PATENT DOCUMENTS

WO    WO-2011055215 A2    5/2011
WO    WO-2013116562 A1    8/2013

OTHER PUBLICATIONS

Schett et al Ther Adv Musculoskel Dis (2010) 2(5) 271-278.*
Sanz et al. (Pharmcology & Therapeutics 106(3), 2005; 269-297).*
Banner, et al., Theophylline and Selective Phosphodiesterase Inhibitors as Anti-Inflammatory Drugs in the Treatment of Bronchial Asthma, European Respiratory Journal, 1995, 8:6:996-1936.
Foukas, et al., Direct Effects of Caffeine and Theophylline on p110delta and Other Phosphoinositide 3-Kinases, Differential Effects on Lipids Kinase and Protein Kinase Activities, Journal of Biological Chemistry, 2002, 227:40:37124-37130.
International Search Report issued in PCT/IB2013/059983, on Jan. 1, 2014.
Hatzelmann, et al., Anti-Inflammatory and Immunomodulatory Potentional of The Novel PDE4 Inhibitor Roflumilast In Vitro, The Journal of Pharmacology and Experimental Therapeutics, 2001, 297:1:267-279.

* cited by examiner

*Primary Examiner* — Shirley V Gembeh
(74) *Attorney, Agent, or Firm* — Blank Rome LLP

(57) ABSTRACT

This present invention relates to a method of treating a autoimmune, respiratory and/or inflammatory disease or condition (e.g., psoriasis, rheumatoid arthritis, asthma, COPD). The method comprises administering a PI3K Delta inhibitor or a dual PI3K Delta-Gamma inhibitor and a PDE4 inhibitor. The present invention also relates to pharmaceutical compositions containing a PI3K Delta or dual PI3K Delta-Gamma inhibitor and a PDE4 inhibitor.

21 Claims, 13 Drawing Sheets

PHARMACEUTICAL COMPOSITIONS CONTAINING A PDE4 INHIBITOR AND A PI3 DELTA OR DUAL PI3 DELTA-GAMMA KINASE INHIBITOR

The present application is the U.S. national stage of International Patent Application No. PCT/IB2013/059983, filed Nov. 7, 2013, which claims the benefit of Indian Patent Application Nos. 2762/CHE/2012, filed Nov. 8, 2012 and 4688/CHE/2012, filed Nov. 8, 2012, each of which is hereby incorporated by reference in its entirety.

FIELD OF THE INVENTION

The present invention relates to a method of treating an autoimmune, respiratory and/or inflammatory disease or condition (such as psoriasis, rheumatoid arthritis, asthma, and COPD) by administering a PI3K Delta inhibitor or a dual PI3K Delta-Gamma inhibitor and a PDE4 inhibitor. The present invention also relates to pharmaceutical compositions containing a PI3K Delta or dual PI3K Delta-Gamma inhibitor and a PDE4 inhibitor.

BACKGROUND OF THE INVENTION

Autoimmune, respiratory and inflammatory diseases such as rheumatoid arthritis (RA), psoriasis, systemic lupus erythematosus (SLE), chronic obstructive pulmonary disease (COPD), and asthma are chronic and often progressive diseases associated with a dysregulated or overactive immune system. The causes and the drivers of these diseases remain ill-defined. They are characterized by complex cellular interactions between multiple inflammatory cells of the innate and adaptive immune system. Accordingly, the heterogeneity and complexity of the disease etiology of these conditions makes the search for new cellular targets challenging, as it is unclear who in the cellular infiltrate is a primary player of the pathology versus an "innocent" bystander.

Rheumatoid arthritis (RA) is a progressive, systemic autoimmune disease characterized by chronic inflammation of multiple joints with associated systemic symptoms such as fatigue. This inflammation causes joint pain, stiffness and swelling, resulting in loss of joint function due to destruction of the bone and cartilage, often leading to progressive disability. Patients with RA also have an increased likelihood of developing other systemic complications such as osteoporosis, anaemia, and other disorders affecting the lungs and skin. The disease also impacts on the average life expectancy, shortening it by three to seven years.

There are a number of treatments available to manage RA. Some address the signs and symptoms of RA, others aim to modify the course of the disease and positively impact the systemic effects of RA, such as fatigue and anaemia.

The current treatments include use of:

Biologics: These are genetically-engineered drugs that target specific cell surface markers or messenger substances in the immune system called cytokines, which are produced by cells in order to regulate other cells during an inflammatory response. An example of a specific cytokine targeted by biologics is tumor necrosis factor alpha (TNFα).

Traditional Disease-Modifying Anti-Rheumatic Drugs (DMARDs): These are non-specific immunosuppressive drugs, intended to combat the signs and symptoms of RA as well as slowing down progressive joint destruction. These treatments are often used in combination with one another, or in combination with a biologic agent, to improve patient response.

Glucocorticoids (Corticosteroids): These are anti-inflammatory drugs related to cortisol, a steroid produced naturally in the body, that work by countering inflammation. However, the side-effects of glucocorticoids, which include hyperglycaemia, osteoporosis, hypertension, weight gain, cataracts, sleep problems, muscle loss, and susceptibility to infections, limit their use.

Non-Steroidal Anti-Inflammatory Drugs (NSAIDs): These manage the signs and symptoms of RA, such as reducing pain, swelling, and inflammation, but do not alter the course of the disease or slow the progression of joint destruction.

There are also a number of RA therapies targeting other components of the immune system. These include biologic treatments targeting alternative cytokines such as interleukin-6 (IL-6) that help to reduce inflammation and the progression of RA in the joints and throughout the body.

Asthma is the most common chronic disease among children and also affects millions of adults. Some 235 million people worldwide suffer from this disease. The causes of asthma, however, are not well understood.

Chronic obstructive pulmonary disease (COPD) is a highly prevalent condition and a major cause of morbidity and mortality worldwide. As the disease progresses, patients with COPD may become prone to frequent exacerbations, resulting in patient anxiety, worsening health status, lung function decline, and increase in mortality rate. These episodes of worsening respiratory function lead to increases in health care utilization, hospital admissions and costs. Worse, frequent exacerbations are associated with a faster decline in lung function, thereby shortening life expectancy.

According to the recommendations of Global Initiative for Chronic Obstructive Lung Disease (GOLD), the first line therapy for COPD are long acting β-agonists, long acting muscarinic antagonist and inhalation corticosteroids. However, these drugs reduce the symptoms and exacerbations associated with the disease, rather than targeting its molecular and cellular basis. Accordingly, there is still a need for further improvement of COPD therapy.

Phosphoinositide-3 kinase (PI3K) belongs to a class of intracellular lipid kinases that phosphorylate the 3 position hydroxyl group of the inositol ring of phosphoinositide lipids (PIs) generating lipid second messengers. There are four claim I PI3K isoforms—alpha, beta, delta, and gamma.

IC87114 (2-((6-amino-9H-purin-9-yl)methyl)-5-methyl-3-o-tolylquinazolin-4(3H)-one) is a specific PI3Kδ inhibitor (Sadhu, J. Immunology, 1; 170(5):2647-2654, 2003; International Publication No. WO 2010/111432 and U.S. Publication Nos. 2010/0249155 and 2010/0168139).

CAL-101 (Idelalisib), TGR-1202, AMG-319, and INCB040093 have been reported as inhibitors of PI3Kδ and are under active clinical development. IPI-145 (duvelisib) and CAL130 have been reported to as dual inhibitors of PI3K δ/γ, IPI-145 is under clinical investigation for cancer and asthma, and for RA in combination with methotrexate.

Phosphodiesterase-4 (PDE4) inhibition is one approach to the treatment of COPD. Roflumilast, a new PDE4 inhibitor, reduces airway inflammation in COPD, as assessed with sputum neutrophil and eosinophil counts. However, roflumilast exhibits dose dependent toxicity which limits the use of roflumilast at higher doses. Calverley, P, Rabe K, et. al, Roflumilast in Symptomatic Chronic Obstructive Pulmonary Disease: Two Randomized Clinical Trials. The Lancet 2009; 374: 685-694 and Fabbri, L, Calverley, P, et. al, Roflumilast in Moderate to Severe Chronic Obstructive Pulmonary Disease Treated with Longacting Bronchodilators: Two Randomized Clinical Trials. The Lancet 2009; 374: 695-703.

In addition, Celgene has shown positive results in two phase III studies for the PDE-4 inhibitor aprelimilast in the treatment of psoriatic arthritis.

Another PDE4 inhibitor is AN2728 from Anacor Pharmaceuticals which has completed phase II studies for atopic dermatitis. Recently, Chiesi Group announced the successful completion of its Phase I trial of CHF6001, an inhaled PDE4 inhibitor being developed for the treatment of inflammatory respiratory disorders, such as chronic obstructive pulmonary disease (COPD) and asthma.

PDE4 inhibitors, however, have a narrow therapeutic window as far as efficacy and toxicity are concerned.

Despite currently available intervention therapies, improved medical treatments for autoimmune disorders, such as RA and psoriasis, and respiratory disorders, such as asthma and COPD, are still needed.

Accordingly, it is an objective of the present invention to provide new pharmaceutical compositions and methods for the treatment of respiratory and/or inflammatory diseases and conditions having enhanced activity.

SUMMARY OF THE INVENTION

The present invention relates to a method of treating an autoimmune, respiratory and/or inflammatory disease or condition, such as rheumatoid arthritis (RA) or chronic obstructive pulmonary disease (COPD). The method involves administering a combination of (i) a PI3K Delta or a dual PI3K Delta and Gamma inhibitor and (ii) a PDE4 inhibitor. It has been surprisingly found that a PI3K Delta or dual PI3K Delta and Gamma inhibitor acts synergistically with a PDE-4 inhibitor (i.e., the combination exhibits an activity which is significantly greater than the activity that would have been expected based on the individual activities of each of the PI3K Delta or dual PI3K Delta and Gamma inhibitor and the PDE-4 inhibitor alone). The PI3K Delta or a dual PI3K Delta and Gamma inhibitor and PDE4 inhibitor may be co-administered (for example, by having both in a single dosage form or administering separate dosage forms simultaneously or sequentially). This combination is particularly useful for treating asthma, allergic rhinitis, non-allergic rhinitis, RA, COPD and atopic dermatitis.

One embodiment is a method of treating an autoimmune, respiratory and/or inflammatory disease or condition (such as RA or COPD) comprising administering to a patient in need thereof a PI3K Delta inhibitor and a PDE4 inhibitor. Preferably, a therapeutically effective amount of the PI3K Delta inhibitor and PDE4 inhibitor are administered.

Another embodiment is a method of treating an autoimmune, respiratory and/or inflammatory disease or condition (such as RA or COPD) comprising administering to a patient in need thereof a dual PI3K Delta and Gamma inhibitor and a PDE4 inhibitor. Preferably, a therapeutically effective amount of the dual PI3K Delta and Gamma inhibitor and PDE4 inhibitor are administered.

Yet another embodiment is a pharmaceutical composition comprising (i) a PI3K Delta or a dual PI3K Delta and Gamma inhibitor and (ii) a PDE4 inhibitor. The pharmaceutical composition may be used for the treatment of autoimmune, respiratory and inflammatory diseases and conditions, such as the treatment of RA and COPD.

In one embodiment, the pharmaceutical composition comprises a PI3K Delta inhibitor and a PDE4 inhibitor. In another embodiment, the pharmaceutical composition comprises a dual PI3K Delta and Gamma inhibitor and a PDE4 inhibitor. In one preferred embodiment, the pharmaceutical composition includes a therapeutically effective amount of the PI3K Delta or dual PI3K Delta and Gamma inhibitor and PDE4 inhibitor.

The methods and compositions described herein allow for the treatment of autoimmune, respiratory and/or inflammatory diseases and conditions with a smaller amount of active agent, thereby allowing for costs savings, reduced side effects and allowing treatment to be continued for a longer period of time in a more efficient way.

In one embodiment, the PI3K Delta or dual PI3K Delta and Gamma inhibitor is a compound of formula (I):

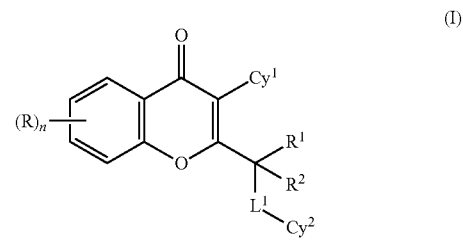

or a tautomer thereof, N-oxide thereof, pharmaceutically acceptable ester thereof, prodrug thereof, or pharmaceutically acceptable salt thereof, wherein each occurrence of R is independently selected from hydrogen, halogen, —OR$^a$, CN, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, and substituted or unsubstituted heterocyclic group;

R$^1$ and R$^2$ may be the same or different and are independently selected from hydrogen, halogen, and substituted or unsubstituted $C_{1-6}$ alkyl, or both R$^1$ and R$^2$ directly bound to a common atom, may be joined to form an oxo group (=O) or a substituted or unsubstituted saturated or unsaturated 3-10 member ring (including the carbon atom to which W and R$^2$ are bound), which may optionally include one or more heteroatoms which may be the same or different and are selected from O, NR$^a$ and S;

Cy$^1$ is a monocyclic group selected from substituted or unsubstituted cycloalkyl, substituted or unsubstituted heterocyclic group, substituted or unsubstituted aryl and substituted or unsubstituted heteroaryl;

Cy$^2$ is selected from a substituted or unsubstituted heterocyclic group, substituted or unsubstituted aryl and substituted or unsubstituted heteroaryl;

L$_1$ is absent or selected from —(CR$^a$R$^b$)$_q$—, —O—, —S(=O)$_q$—, —NR$^a$— or —C(=Y)—;

each occurrence of R$^a$ and R$^b$ may be the same or different and are independently selected from hydrogen, halogen, hydroxy, cyano, substituted or unsubstituted (C$_{1-6}$)alkyl, —NR$^c$R$^d$ (wherein R$^c$ and R$^d$ are independently hydrogen, halogen, hydroxy, cyano, substituted or unsubstituted (C$_{1-6}$)alkyl, and (C$_{1-6}$)alkoxy) and —OR$^c$ (wherein R$^c$ is substituted or unsubstituted (C$_{1-6}$)alkyl) or when R$^a$ and R$^b$ are directly bound to a common atom, they may be joined to form an oxo group (=O) or form a substituted or unsubstituted saturated or unsaturated 3-10 member ring (including the common atom to which R$^a$ and R$^b$ are directly bound), which may optionally include one or more heteroatoms which may be the same or different and are selected from O, NR$^d$ (wherein R$^d$ is hydrogen or substituted or unsubstituted (C$_{1-6}$)alkyl) or S;

Y is selected from O, S, and NR$^a$;

n is 1, 2, 3 or 4; and q is 0, 1 or 2.

In one embodiment, the compound of formula (I) is a compound of formula (II):

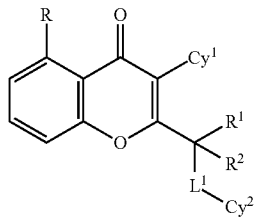

(II)

or a tautomer thereof, N-oxide thereof, pharmaceutically acceptable ester thereof, prodrug thereof, or pharmaceutically acceptable salt thereof, wherein R, R$^1$, R$^2$, L$_1$, Cy$^1$ and Cy$^2$ are as described above for formula (I).

In further embodiments, the compound of formula (I) is selected from a compound of formulas (IA-I), (IA-II), (IA-III) and (IA-IV):

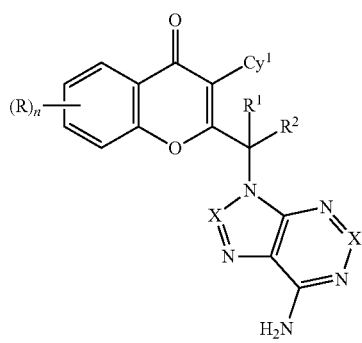

(IA-I)

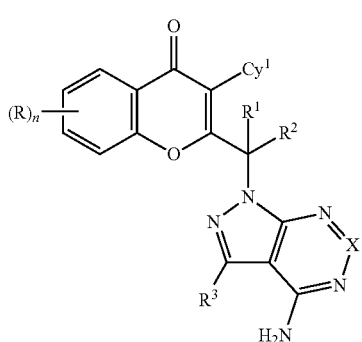

(IA-II)

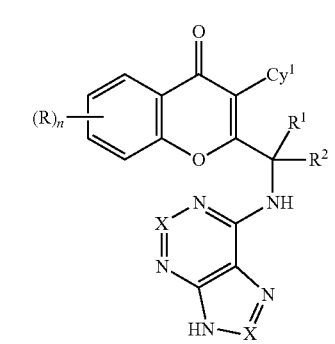

(IA-III)

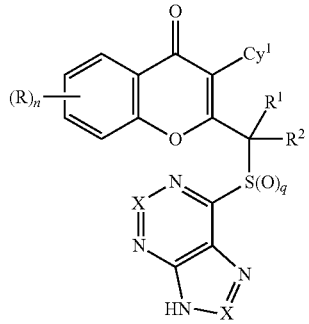

(IA-IV)

or a tautomer thereof, N-oxide thereof, pharmaceutically acceptable ester thereof, prodrug thereof, or pharmaceutically acceptable salt thereof, wherein R, Cy$^1$, R$^1$, R$^2$, n and q are as defined above;

each occurrence of X is independently selected from CR$^3$ or N; and each occurrence of R$^3$ is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenylalkyl substituted or unsubstituted cycloalkenyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, —COOR$^x$, —C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$, —NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted heteroaryl, substituted or unsubstituted heteroarylalkyl, substituted or unsubstituted heterocyclic ring, substituted or unsubstituted heterocyclylalkyl ring, or substituted or unsubstituted amino, or any two of R$^x$, R$^y$ and R$^z$ may be joined to form a substituted or unsubstituted saturated or unsaturated 3-10 membered ring, which may optionally include heteroatoms which may be the same or different and are selected from O, NR$^f$ (wherein R$^f$ is hydrogen or substituted or unsubstituted alkyl) or S.

In a preferred embodiment, the present invention relates to method of treating an autoimmune, respiratory and/or inflammatory disease or condition comprising administering a combination of a PI3K Delta or dual PI3K Delta and Gamma inhibitor and a PDE4 inhibitor, where the PI3K Delta or dual PI3K Delta and Gamma inhibitor is a compound of formula (I), (II), (IA-I), (IA-II), (IA-HI), or (IA-IV), as described above.

In another preferred embodiment, the present invention relates to a pharmaceutical composition comprising a PI3K Delta or dual PI3K Delta and Gamma inhibitor and a PDE4 inhibitor, where the PI3K Delta or dual PI3K Delta and Gamma inhibitor is a compound of formula (I), (II), (IA-I), (IA-II), (IA-III), or (IA-IV), as described above.

In a preferred embodiment, the compound of formula (I) is selected from:

2-[(6-Amino-9H-purin-9-yl)methyl]-6-bromo-3-phenyl-4H-chromen-4-one;

6-Bromo-2-(morpholinomethyl)-3-phenyl-4H-chromen-4-one;

6-Bromo-2-(morpholinomethyl)-3-phenyl-4H-chromen-4-one hydrochloride;

2-[(6-Amino-9H-purin-9-yl)methyl]-3-phenyl-4H-chromen-4-one;

2-(Morpholinomethyl)-3-phenyl-4H-chromen-4-one;

2-(Morpholinomethyl)-3-phenyl-4H-chromen-4-one hydrochloride;

2-[(1H-Benzo[d]imidazol-1-yl)methyl]-6-bromo-3-phenyl-4H-chromen-4-one;

6-Bromo-2-[(4-methyl-1H-benzo[d]imidazol-1-yl)methyl]-3-phenyl-4H-chromen-4-one;

2-[(1H-benzo[d]imidazol-1-yl)methyl]-3-phenyl-4H-chromen-4-one;

2-[(4-methyl-1H-benzo[d]imidazol-1-yl)methyl]-3-phenyl-4H-chromen-4-one;

2-[(6-Chloro-9H-purin-9-yl)methyl]-3-phenyl-4H-chromen-4-one;

6-Bromo-2-[(6-chloro-9H-purin-9-yl)methyl]-3-phenyl-4H-chromen-4-one;

2-((9H-Purin-6-ylthio)methyl)-3-phenyl-4H-chromen-4-one;

2-[(1H-Imidazol-1-yl)methyl]-3-phenyl-4H-chromen-4-one;

2-[(9H-Purin-6-ylthio)methyl]-6-bromo-3-phenyl-4H-chromen-4-one;

2-((4-Amino-1H-pyrazolo[3,4-d]pyrimidin-1-yl)methyl)-6-bromo-3-phenyl-4H-Chromen-4-one;

2-[(6-Amino-9H-purin-9-yl)methyl]-6-bromo-3-(4-fluorophenyl)-4H-chromen-4-one;

2-[(6-Amino-9H-purin-9-yl)methyl]-3-(4-fluorophenyl)-4H-chromen-4-one;

6-Bromo-3-(4-fluorophenyl)-2-(morpholinomethyl)-4H-chromen-4-one;

6-Bromo-3-(4-fluorophenyl)-2-(morpholinomethyl)-4H-chromen-4-one hydrochloride;

3-(4-fluorophenyl)-2-(morpholinomethyl)-4H-chromen-4-one;

3-(4-fluorophenyl)-2-(morpholinomethyl)-4H-chromen-4-one hydrochloride;

2-[(6-Amino-9H-purin-9-yl)methyl]-6-bromo-3-o-tolyl-4H-chromen-4-one;

7-[(6-Bromo-4-oxo-3-phenyl-4H-chromen-2-yl)methyl]-1,3-dimethyl-1H-purine-2,6(3H,7H)-dione;

2-(1-(6-Amino-9H-purin-9-yl)ethyl)-6-bromo-3-phenyl-4H-chromen-4-one;

2-(1-(9H-Purin-6-ylthio)ethyl)-6-bromo-3-phenyl-4H-chromen-4-one;

2-(1-(6-Amino-9H-purin-9-yl)ethyl)-3-phenyl-4H-chromen-4-one;

(S)-2-(1-(9H-purin-6-ylamino)ethyl)-6-bromo-3-phenyl-4H-chromen-4-one;

2-((9H-purin-6-ylamino)methyl)-6-bromo-3-phenyl-4H-chromen-4-one;

2-(1-(4-amino-1H-pyrazolo[3,4-d]pyrimidin-1-yl)ethyl)-6-bromo-3-phenyl-4H-chromen-4-one;

2-((6-Amino-9H-purin-9-yl)methyl)-6-methoxy-3-phenyl-4H-chromen-4-one;

2-(1-(6-Amino-9H-purin-9-yl)ethyl)-6-bromo-3-(2-fluorophenyl)-4H-chromen-4-one;

2-((6-Amino-9H-purin-9-yl)methyl)-6-bromo-3-(2-fluorophenyl)-4H-chromen-4-one;

2-(1-(4-Amino-1H-pyrazolo[3,4-d]pyrimidin-1-yl)ethyl)-3-phenyl-4H-chromen-4-one;

2-(1-(6-Amino-9H-purin-9-yl)propyl)-3-phenyl-4H-chromen-4-one;

2-(1-(6-Amino-9H-purin-9-yl)ethyl)-3-(3-fluorophenyl)-4H-chromen-4-one;

2-((6-Amino-9H-purin-9-yl)methyl)-3-(2-fluorophenyl)-4H-chromen-4-one;

2-(1-(6-Amino-9H-purin-9-yl)ethyl)-3-(2-fluorophenyl)-4H-chromen-4-one;

2-(1-(6-Amino-9H-purin-9-yl) propyl)-3-(2-fluorophenyl)-4H-chromen-4-one;

2-(1-(6-amino-9H-purin-9-yl) propyl)-3-(3-fluorophenyl)-4H-chromen-4-one;

2-(1-(6-Amino-9H-purin-9-yl) propyl)-3-(4-fluorophenyl)-4H-chromen-4-one;

2-(1-(6-amino-9H-purin-9-yl) propyl)-6-fluoro-3-phenyl-4H-chromen-4-one;

2-(1-(6-Amino-9H-purin-9-yl)ethyl)-3-(4-fluorophenyl)-4H-chromen-4-one;

2-(1-(6-Amino-9H-purin-9-yl)ethyl)-6-fluoro-3-phenyl-4H-chromen-4-one;

2-(1-(4-Amino-3-(3-methoxyphenyl)-1H-pyrazolo[3,4-d]pyrimidin-1-yl)ethyl)-3-phenyl-4H-chromen-4-one;

2-(1-(4-Amino-3-(3-hydroxyphenyl)-1H-pyrazolo[3,4-d]pyrimidin-1-yl)ethyl)-3-phenyl-4H-chromen-4-one;

2-((9H-purin-6-ylamino)methyl)-3-phenyl-4H-chromen-4-one;

2-(1-(6-Amino-9H-purin-9-yl)ethyl)-3-o-tolyl-4H-chromen-4-one;

2-((9H-purin-6-ylamino)methyl)-3-(2-fluorophenyl)-4H-chromen-4-one;

2-((9H-purin-6-ylamino)methyl)-3-(3-fluorophenyl)-4H-chromen-4-one;

(S)-2-(1-(9H-purin-6-ylamino)ethyl)-3-(3-fluorophenyl)-4H-chromen-4-one;

2-(1-(6-amino-9H-purin-9-yl)ethyl)-6-fluoro-3-(2-fluorophenyl)-4H-chromen-4-one;

2-(1-(6-Amino-9H-purin-9-yl)ethyl)-3-(3,5-difluorophenyl)-4H-chromen-4-one;

2-(1-(6-amino-9H-purin-9-yl)ethyl)-6-fluoro-3-(3-fluorophenyl)-4H-chromen-4-one;

2-(1-(4-amino-3-(3-methoxyphenyl)-1H-pyrazolo[3,4-d]pyrimidin-1-yl)ethyl)-3-(3-fluorophenyl)-4H-chromen-4-one;

2-(1-(4-amino-3-(3-hydroxyphenyl)-1H-pyrazolo[3,4-d]pyrimidin-1-yl)ethyl)-3-(3-fluorophenyl)-4H-chromen-4-one;

2-((4-Amino-3-(3-methoxyphenyl)-1H-pyrazolo[3,4-d]pyrimidin-1-yl)methyl)-3-phenyl-4H-chromen-4-one;

2-((4-Amino-3-(3-hydroxyphenyl)-1H-pyrazolo[3,4-d]pyrimidin-1-yl)methyl)-3-phenyl-4H-chromen-4-one;

2-((4-amino-3-(3-methoxyphenyl)-1H-pyrazolo[3,4-d]pyrimidin-1-yl)methyl)-3-(3-fluorophenyl)-4H-chromen-4-one;

2-((4-amino-3-(3-hydroxyphenyl)-1H-pyrazolo[3,4-d]pyrimidin-1-yl)methyl)-3-(3-fluorophenyl)-4H-chromen-4-one;

(R)-2-(1-(9H-purin-6-ylamino)ethyl)-3-(3-fluorophenyl)-4H-chromen-4-one;

(S)-2-(1-(9H-purin-6-ylamino)ethyl)-6-fluoro-3-phenyl-4H-chromen-4-one;

2-((4-Amino-3-iodo-1H-pyrazolo[3,4-d]pyrimidin-1-yl)methyl)-3-phenyl-4H-chromen-4-one;

2-(1-(4-amino-3-iodo-1H-pyrazolo[3,4-d]pyrimidin-1-yl)ethyl)-3-phenyl-4H-chromen-4-one;

2-(1-(4-amino-3-iodo-1H-pyrazolo[3,4-d]pyrimidin-1-yl)ethyl)-3-(3-fluorophenyl)-4H-chromen-4-one;

2-((4-amino-3-iodo-1H-pyrazolo[3,4-d]pyrimidin-1-yl)methyl)-6-fluoro-3-phenyl-4H-chromen-4-one;

2-(1-(4-amino-3-iodo-1H-pyrazolo[3,4-d]pyrimidin-1-yl)ethyl)-6-fluoro-3-phenyl-4H-chromen-4-one;

2-(1-(4-amino-3-iodo-1H-pyrazolo[3,4-d]pyrimidin-1-yl)ethyl)-6-fluoro-3-(3-fluorophenyl)-4H-chromen-4-one;

2-(1-(4-amino-3-iodo-1H-pyrazolo[3,4-d]pyrimidin-1-yl)propyl)-3-(3-fluorophenyl)-4H-chromen-4-one;

2-((4-amino-3-(pyridin-3-yl)-1H-pyrazolo[3,4-d]pyrimidin-1-yl)methyl)-3-phenyl-4H-chromen-4-one;

2-((4-amino-3-(3-hydroxyprop-1-ynyl)-1H-pyrazolo[3,4-d]pyrimidin-1-yl)methyl)-3-phenyl-4H-chromen-4-one;

2-((4-amino-3-(1H-pyrazol-4-yl)-1H-pyrazolo[3,4-d]pyrimidin-1-yl)methyl)-3-phenyl-4H-chromen-4-one;

2-((4-amino-3-(3-(hydroxymethyl)phenyl)-1H-pyrazolo[3,4-d]pyrimidin-1-yl)methyl)-3-phenyl-4H-chromen-4-one;

2-((4-amino-3-(1H-indazol-4-yl)-1H-pyrazolo[3,4-d]pyrimidin-1-yl)methyl)-3-phenyl-4H-chromen-4-one;

2-((4-amino-3-(3-fluorophenyl)-1H-pyrazolo[3,4-d]pyrimidin-1-yl)methyl)-3-phenyl-4H-chromen-4-one 2-((4-amino-3-(3-hydroxypropyl)-1H-pyrazolo[3,4-d]pyrimidin-1-yl)methyl)-3-phenyl-4H-chromen-4-one;

N-(3-(4-amino-1-((4-oxo-3-phenyl-4H-chromen-2-yl)methyl)-1H-pyrazolo[3,4-d]pyrimidin-3-yl)phenyl) acetamide;

2-((4-amino-3-(3-fluoro-5-methoxyphenyl)-1H-pyrazolo[3,4-d]pyrimidin-1-yl)methyl)-3-phenyl-4H-chromen-4-one;

2-((4-amino-3-(3-fluoro-5-hydroxyphenyl)-1H-pyrazolo[3,4-d]pyrimidin-1-yl)methyl)-3-phenyl-4H-chromen-4-one;

2-((4-amino-3-(3-fluoro-5-methoxyphenyl)-1H-pyrazolo[3,4-d]pyrimidin-1-yl)methyl)-3-(3-fluorophenyl)-4H-chromen-4-one;

2-((4-amino-3-(3-fluoro-5-hydroxyphenyl)-1H-pyrazolo[3,4-d]pyrimidin-1-yl)methyl)-3-(3-fluorophenyl)-4H-chromen-4-one;

2-(1-(4-amino-3-(1H-pyrazol-4-yl)-1H-pyrazolo[3,4-d]pyrimidin-1-yl)ethyl)-3-phenyl-4H-chromen-4-one;

2-(1-(4-amino-3-(1H-indazol-6-yl)-1H-pyrazolo[3,4-d]pyrimidin-1-yl)ethyl)-3-phenyl-4H-chromen-4-one;

2-(1-(4-amino-3-(3-hydroxy-3-methylbut-1-ynyl)-1H-pyrazolo[3,4-d]pyrimidin-1-yl)ethyl)-3-phenyl-4H-chromen-4-one;

2-(1-(4-amino-3-(1H-pyrazol-4-yl)-1H-pyrazolo[3,4-d]pyrimidin-1-yl)ethyl)-3-(3-fluorophenyl)-4H-chromen-4-one;

(S)-2-(1-(9H-purin-6-ylamino)ethyl)-3-phenyl-4H-chromen-4-one;

(S)-2-(1-(9H-purin-6-ylamino)ethyl)-6-fluoro-3-(3-fluorophenyl)-4H-chromen-4-one;

2-((4-amino-3-(1H-indazol-6-yl)-1H-pyrazolo[3,4-d]pyrimidin-1-yl)methyl)-3-phenyl-4H-chromen-4-one;

2-(1-(4-amino-3-(3-fluoro-5-methoxyphenyl)-1H-pyrazolo[3,4-d]pyrimidin-1-yl)ethyl)-3-(3-fluorophenyl)-4H-chromen-4-one;

2-(1-(4-amino-3-(3-fluoro-5-hydroxyphenyl)-1H-pyrazolo[3,4-d]pyrimidin-1-yl)ethyl)-3-(3-fluorophenyl)-4H-chromen-4-one;

2-(1-(4-amino-3-(1H-indazol-4-yl)-1H-pyrazolo[3,4-d]pyrimidin-1-yl)ethyl)-3-(3-fluorophenyl)-4H-chromen-4-one;

2-(1-(4-amino-3-(3,5-dimethyl-1H-pyrazol-4-yl)-1H-pyrazolo[3,4-d]pyrimidin-1-yl)ethyl)-3-(3-fluorophenyl)-4H-chromen-4-one;

2-(1-(4-amino-3-(3-methyl-1H-indazol-6-yl)-1H-pyrazolo[3,4-d]pyrimidin-1-yl)ethyl)-3-(3-fluorophenyl)-4H-chromen-4-one;

2-(1-(4-amino-3-(1H-indazol-6-yl)-1H-pyrazolo[3,4-d]pyrimidin-1-yl)ethyl)-3-(3-fluorophenyl)-4H-chromen-4-one;

2-(1-(4-amino-3-(2-(hydroxymethyl)phenyl)-1H-pyrazolo[3,4-d]pyrimidin-1-yl)ethyl)-3-(3-fluorophenyl)-4H-chromen-4-one;

2-(1-(4-amino-3-(4-fluoro-3-methoxyphenyl)-1H-pyrazolo[3,4-d]pyrimidin-1-yl)ethyl)-3-(3-fluorophenyl)-4H-chromen-4-one;

2-(1-(4-amino-3-(4-fluoro-3-hydroxyphenyl)-1H-pyrazolo[3,4-d]pyrimidin-1-yl)ethyl)-3-(3-fluorophenyl)-4H-chromen-4-one;

2-(1-(4-amino-3-(3-hydroxyprop-1-ynyl)-1H-pyrazolo[3,4-d]pyrimidin-1-yl)ethyl)-3-(3-fluorophenyl)-4H-chromen-4-one;

2-(1-(4-amino-3-(3-fluoro-4-methoxyphenyl)-1H-pyrazolo[3,4-d]pyrimidin-1-yl)ethyl)-3-(3-fluorophenyl)-4H-chromen-4-one;

2-(1-(4-amino-3-(3-fluoro-4-hydroxyphenyl)-1H-pyrazolo[3,4-d]pyrimidin-1-yl)ethyl)-3-(3-fluorophenyl)-4H-chromen-4-one;

2-(1-(4-amino-3-(3-chloro-5-methoxyphenyl)-1H-pyrazolo[3,4-d]pyrimidin-1-yl)ethyl)-3-(3-fluorophenyl)-4H-chromen-4-one;

2-(1-(4-amino-3-(3-chloro-5-hydroxyphenyl)-1H-pyrazolo[3,4-d]pyrimidin-1-yl)ethyl)-3-(3-fluorophenyl)-4H-chromen-4-one;

2-(1-(4-amino-3-(3-(trifluoromethoxy)phenyl)-1H-pyrazolo[3,4-d]pyrimidin-1-yl)ethyl)-3-(3-fluorophenyl)-4H-chromen-4-one;

2-(1-(4-amino-3-(4-methoxyphenyl)-1H-pyrazolo[3,4-d]pyrimidin-1-yl)ethyl)-3-(3-fluorophenyl)-4H-chromen-4-one;

2-(1-(4-amino-3-(4-hydroxyphenyl)-1H-pyrazolo[3,4-d]pyrimidin-1-yl)ethyl)-3-(3-fluorophenyl)-4H-chromen-4-one;

2-((6-amino-9H-purin-9-yl)methyl)-3-(3-fluorophenyl)-4H-chromen-4-one;

2-(1-(4-amino-3-(4-fluoro-2-methoxyphenyl)-1H-pyrazolo[3,4-d]pyrimidin-1-yl)ethyl)-3-(3-fluorophenyl)-4H-chromen-4-one;

2-(1-(4-amino-3-(4-fluoro-2-hydroxyphenyl)-1H-pyrazolo[3,4-d]pyrimidin-1-yl)ethyl)-3-(3-fluorophenyl)-4H-chromen-4-one;

2-((4-amino-3-(3-aminophenyl)-1H-pyrazolo[3,4-d]pyrimidin-1-yl)methyl)-3-phenyl-4H-chromen-4-one;

2-((4-amino-3-(3-methyl-1H-indazol-6-yl)-1H-pyrazolo[3,4-d]pyrimidin-1-yl)methyl)-3-phenyl-4H-chromen-4-one;

2-(1-(4-amino-3-(2-aminopyrimidin-5-yl)-1H-pyrazolo[3,4-d]pyrimidin-1-yl)ethyl)-3-(3-fluorophenyl)-4H-chromen-4-one;

2-(1-(4-amino-3-(1H-indol-6-yl)-1H-pyrazolo[3,4-d]pyrimidin-1-yl)ethyl)-3-(3-fluorophenyl)-4H-chromen-4-one;

2-(1-(4-amino-3-(4-chloro-3-methoxyphenyl)-1H-pyrazolo[3,4-d]pyrimidin-1-yl)ethyl)-3-(3-fluorophenyl)-4H-chromen-4-one;

2-(1-(4-amino-3-(4-chloro-3-hydroxyphenyl)-1H-pyrazolo[3,4-d]pyrimidin-1-yl)ethyl)-3-(3-fluorophenyl)-4H-chromen-4-one;

2-(1-(4-amino-3-(2-chloro-5-methoxyphenyl)-1H-pyrazolo[3,4-d]pyrimidin-1-yl)ethyl)-3-(3-fluorophenyl)-4H-chromen-4-one;

2-(1-(4-amino-3-(2-chloro-5-hydroxyphenyl)-1H-pyrazolo[3,4-d]pyrimidin-1-yl)ethyl)-3-(3-fluorophenyl)-4H-chromen-4-one;

2-(1-(4-amino-3-(3,4-dimethoxyphenyl)-1H-pyrazolo[3,4-d]pyrimidin-1-yl)ethyl)-3-(3-fluorophenyl)-4H-chromen-4-one;

2-(1-(4-amino-3-(3,4-dihydroxyphenyl)-1H-pyrazolo[3,4-d]pyrimidin-1-yl)ethyl)-3-(3-fluorophenyl)-4H-chromen-4-one;

2-((4-amino-3-(3-methyl-1H-indazol-6-yl)-1H-pyrazolo[3,4-d]pyrimidin-1-yl)methyl)-3-(3-fluorophenyl)-4H-chromen-4-one;

2-(1-(4-amino-3-(1H-indol-5-yl)-1H-pyrazolo[3,4-d]pyrimidin-1-yl)ethyl)-3-(3-fluorophenyl)-4H-chromen-4-one;

2-(1-(4-Amino-3-(3-methyl-1H-indol-5-yl)-1H-pyrazolo[3,4-d]pyrimidin-1-yl)ethyl)-3-(3-fluorophenyl)-4H-chromen-4-one;

tert-butyl-(5-(4-amino-1-(1-(3-(3-fluorophenyl)-4-oxo-4H-chromen-2-yl)ethyl)-1H-pyrazolo[3,4-d]pyrimidin-3-yl)thiophen-2-yl)methylcarbamate 2-(1-(4-amino-3-(5-(aminomethyl)thiophen-2-yl)-1H-pyrazolo[3,4-d]pyrimidin-1-yl)ethyl)-3-(3-fluorophenyl)-4H-chromen-4-one;

2-((4-amino-3-(3-methyl-1H-indazol-6-yl)-1H-pyrazolo[3,4-d]pyrimidin-1-yl)methyl)-6-fluoro-3-phenyl-4H-chromen-4-one;

2-(1-(4-amino-3-(3-methyl-1H-indazol-6-yl)-1H-pyrazolo[3,4-d]pyrimidin-1-yl)ethyl)-3-phenyl-4H-chromen-4-one;

2-(1-(4-amino-3-(3-methyl-1H-indazol-6-yl)-1H-pyrazolo[3,4-d]pyrimidin-1-yl)ethyl)-6-fluoro-3-phenyl-4H-chromen-4-one;

2-(1-(4-amino-3-(3-methyl-1H-indazol-5-yl)-1H-pyrazolo[3,4-d]pyrimidin-1-yl)ethyl)-3-(3-fluorophenyl)-4H-chromen-4-one;

N-(4-(4-amino-1-(1-(3-(3-fluorophenyl)-4-oxo-4H-chromen-2-yl)ethyl)-1H-pyrazolo[3,4-d]pyrimidin-3-yl)phenyl) acetamide;

2-(1-(4-amino-3-(4-aminophenyl)-1H-pyrazolo[3,4-d]pyrimidin-1-yl)ethyl)-3-(3-fluorophenyl)-4H-chromen-4-one;

2-(1-(4-amino-3-(3-methyl-1H-indazol-6-yl)-1H-pyrazolo[3,4-d]pyrimidin-1-yl)ethyl)-6-fluoro-3-(3-fluorophenyl)-4H-chromen-4-one;

2-(1-(4-amino-3-(2,3-dihydrobenzofuran-5-yl)-1H-pyrazolo[3,4-d]pyrimidin-1-yl)ethyl)-3-(3-fluorophenyl)-4H-chromen-4-one;

2-(1-(4-amino-3-(3-ethyl-1H-indazol-6-yl)-1H-pyrazolo[3,4-d]pyrimidin-1-yl)ethyl)-3-(3-fluorophenyl)-4H-chromen-4-one;

2-(1-(4-amino-3-(3-methyl-1H-indol-6-yl)-1H-pyrazolo[3,4-d]pyrimidin-1-yl)ethyl)-3-(3-fluorophenyl)-4H-chromen-4-one;

2-(1-(4-amino-3-(2-methoxypyrimidin-5-yl)-1H-pyrazolo[3,4-d]pyrimidin-1-yl)ethyl)-3-(3-fluorophenyl)-4H-chromen-4-one;

4-(4-amino-1-(1-(3-(3-fluorophenyl)-4-oxo-4H-chromen-2-yl)ethyl)-1H-pyrazolo[3,4-d]pyrimidin-3-yl)thiophene-2-carbaldehyde;

2-(1-(4-amino-3-(5-(hydroxymethyl)thiophen-3-yl)-1H-pyrazolo[3,4-d]pyrimidin-1-yl)ethyl)-3-(3-fluorophenyl)-4H-chromen-4-one;

2-(1-(4-amino-3-(2-methyl-1H-benzo[d]imidazol-5-yl)-1H-pyrazolo[3,4-d]pyrimidin-1-yl)ethyl)-3-(3-fluorophenyl)-4H-chromen-4-one;

2-(1-(4-amino-3-(3-methyl-1H-indazol-6-yl)-1H-pyrazolo[3,4-d]pyrimidin-1-yl) propyl)-3-(3-fluorophenyl)-4H-chromen-4-one;

2-(1-(4-amino-3-(3-methyl-1H-indol-6-yl)-1H-pyrazolo[3,4-d]pyrimidin-1-yl)ethyl)-3-(3-fluorophenyl)-4H-chromen-4-one;

2-((6-amino-9H-purin-9-yl)methyl)-6-fluoro-3-phenyl-4H-chromen-4-one;

2-((6-amino-9H-purin-9-yl)methyl)-6-fluoro-3-(3-fluorophenyl)-4H-chromen-4-one;

2-((4-amino-3-(3-fluoro-5-methoxyphenyl)-1H-pyrazolo[3,4-d]pyrimidin-1-yl)methyl)-6-fluoro-3-(3-fluorophenyl)-4H-chromen-4-one;

2-((4-amino-3-(3-fluoro-5-hydroxyphenyl)-1H-pyrazolo[3,4-d]pyrimidin-1-yl)methyl)-6-fluoro-3-(3-fluorophenyl)-4H-chromen-4-one;

2-(1-(4-amino-3-(3-methoxyphenyl)-1H-pyrazolo[3,4-d]pyrimidin-1-yl)ethyl)-6-fluoro-3-(3-fluorophenyl)-4H-chromen-4-one;

2-(1-(4-amino-3-(3-hydroxyphenyl)-1H-pyrazolo[3,4-d]pyrimidin-1-yl)ethyl)-6-fluoro-3-(3-fluorophenyl)-4H-chromen-4-one;

2-((9H-purin-6-ylamino)methyl)-6-fluoro-3-(3-fluorophenyl)-4H-chromen-4-one;

2-((9H-purin-6-ylamino)methyl)-6-fluoro-3-phenyl-4H-chromen-4-one;

(R)-2-(1-(9H-purin-6-ylamino)ethyl)-6-fluoro-3-(3-fluorophenyl)-4H-chromen-4-one;

2-((4-amino-3-(1H-pyrazol-4-yl)-1H-pyrazolo[3,4-d]pyrimidin-1-yl)methyl)-6-fluoro-3-phenyl-4H-chromen-4-one;

2-(1-(4-amino-3-(3,5-difluoro-4-methoxyphenyl)-1H-pyrazolo[3,4-d]pyrimidin-1-yl)ethyl)-3-(3-fluorophenyl)-4H-chromen-4-one;

2-(1-(4-amino-3-(3,5-difluoro-4-hydroxyphenyl)-1H-pyrazolo[3,4-d]pyrimidin-1-yl)ethyl)-3-(3-fluorophenyl)-4H-chromen-4-one;

2-((4-amino-3-(3,5-difluoro-4-methoxyphenyl)-1H-pyrazolo[3,4-d]pyrimidin-1-yl)methyl)-6-fluoro-3-(3-fluorophenyl)-4H-chromen-4-one;

2-((4-amino-3-(3,5-difluoro-4-hydroxyphenyl)-1H-pyrazolo[3,4-d]pyrimidin-1-yl)methyl)-6-fluoro-3-(3-fluorophenyl)-4H-chromen-4-one;

(+)-2-(1-(4-amino-3-(3-methyl-1H-indazol-6-yl)-1H-pyrazolo[3,4-d]pyrimidin-1-yl)ethyl)-3-(3-fluorophenyl)-4H-chromen-4-one;

(−)-2-(1-(4-amino-3-(3-methyl-1H-indazol-6-yl)-1H-pyrazolo[3,4-d]pyrimidin-1-yl)ethyl)-3-(3-fluorophenyl)-4H-chromen-4-one;

2-(1-(4-amino-3-(3,5-dimethoxyphenyl)-1H-pyrazolo[3,4-d]pyrimidin-1-yl)ethyl)-3-(3-fluorophenyl)-4H-chromen-4-one;

2-(1-(4-amino-3-(4-methoxy-3,5-dimethylphenyl)-1H-pyrazolo[3,4-d]pyrimidin-1-yl)ethyl)-3-(3-fluorophenyl)-4H-chromen-4-one;

2-(1-(4-amino-3-(2-fluoro-5-isopropoxyphenyl)-1H-pyrazolo[3,4-d]pyrimidin-1-yl)ethyl)-3-(3-fluorophenyl)-4H-chromen-4-one;

2-(1-(4-amino-3-(2,3-dihydrobenzo[b][1,4]dioxin-6-yl)-1H-pyrazolo[3,4-d]pyrimidin-1-yl)ethyl)-3-(3-fluorophenyl)-4H-chromen-4-one;

2-(1-(4-amino-3-(1-benzyl-1H-pyrazol-4-yl)-1H-pyrazolo[3,4-d]pyrimidin-1-yl)ethyl)-3-(3-fluorophenyl)-4H-chromen-4-one;

2-(1-(4-amino-3-(2-methylpyridin-4-yl)-1H-pyrazolo[3,4-d]pyrimidin-1-yl)ethyl)-3-(3-fluorophenyl)-4H-chromen-4-one;

2-(1-(4-amino-3-(3,4-dihydro-2H-benzo[b][1,4]dioxepin-7-yl)-1H-pyrazolo[3,4-d]pyrimidin-1-yl)ethyl)-3-(3-fluorophenyl)-4H-chromen-4-one;

2-(1-(4-amino-3-(6-morpholinopyridin-3-yl)-1H-pyrazolo[3,4-d]pyrimidin-1-yl)ethyl)-3-(3-fluorophenyl)-4H-chromen-4-one;

2-(1-(4-amino-3-(dibenzo[b, d]furan-4-yl)-1H-pyrazolo[3,4-d]pyrimidin-1-yl)ethyl)-3-(3-fluorophenyl)-4H-chromen-4-one;

2-(1-(4-amino-3-(4-phenoxyphenyl)-1H-pyrazolo[3,4-d]pyrimidin-1-yl)ethyl)-3-(3-fluorophenyl)-4H-chromen-4-one;

2-(1-(4-amino-3-(4-(benzyloxy)-3-chlorophenyl)-1H-pyrazolo[3,4-d]pyrimidin-1-yl)ethyl)-3-(3-fluorophenyl)-4H-chromen-4-one;

2-(1-(4-amino-3-(3-chloro-4-isopropoxyphenyl)-1H-pyrazolo[3,4-d]pyrimidin-1-yl)ethyl)-3-(3-fluorophenyl)-4H-chromen-4-one;

2-(1-(4-amino-3-(3-(dimethylamino)phenyl)-1H-pyrazolo[3,4-d]pyrimidin-1-yl)ethyl)-3-(3-fluorophenyl)-4H-chromen-4-one;

2-(1-(4-amino-3-(4-ethoxy-3-fluorophenyl)-1H-pyrazolo[3,4-d]pyrimidin-1-yl)ethyl)-3-(3-fluorophenyl)-4H-chromen-4-one;

2-(1-(4-amino-3-(4-isopropoxyphenyl)-1H-pyrazolo[3,4-d]pyrimidin-1-yl)ethyl)-3-(3-fluorophenyl)-4H-chromen-4-one;

2-(1-(4-amino-3-(4-(trifluoromethoxy)phenyl)-1H-pyrazolo[3,4-d]pyrimidin-1-yl)ethyl)-3-(3-fluorophenyl)-4H-chromen-4-one;

2-(1-(3-(4-acetylphenyl)-4-amino-1H-pyrazolo[3,4-d]pyrimidin-1-yl)ethyl)-3-(3-fluorophenyl)-4H-chromen-4-one;

2-(1-(4-amino-3-(4-(benzyloxy)phenyl)-1H-pyrazolo[3,4-d]pyrimidin-1-yl)ethyl)-3-(3-fluorophenyl)-4H-chromen-4-one;

2-(1-(4-amino-3-(4-(dimethylamino)phenyl)-1H-pyrazolo[3,4-d]pyrimidin-1-yl)ethyl)-3-(3-fluorophenyl)-4H-chromen-4-one;

2-(1-(4-amino-3-(4-(methylsulfonyl)phenyl)-1H-pyrazolo[3,4-d]pyrimidin-1-yl)ethyl)-3-(3-fluorophenyl)-4H-chromen-4-one;

2-(1-(4-amino-3-(3-ethoxyphenyl)-1H-pyrazolo[3,4-d]pyrimidin-1-yl)ethyl)-3-(3-fluorophenyl)-4H-chromen-4-one;

2-(1-(4-amino-3-(benzo[b]thiophen-2-yl)-1H-pyrazolo[3,4-d]pyrimidin-1-yl)ethyl)-3-(3-fluorophenyl)-4H-chromen-4-one;

2-(1-(4-amino-3-(5-chlorothiophen-2-yl)-1H-pyrazolo[3,4-d]pyrimidin-1-yl)ethyl)-3-(3-fluorophenyl)-4H-chromen-4-one;

2-(1-(4-amino-3-(3,5-dimethylisoxazol-4-yl)-1H-pyrazolo[3,4-d]pyrimidin-1-yl)ethyl)-3-(3-fluorophenyl)-4H-chromen-4-one;

2-(1-(4-amino-3-(3-propoxyphenyl)-1H-pyrazolo[3,4-d]pyrimidin-1-yl)ethyl)-3-(3-fluorophenyl)-4H-chromen-4-one;

2-(1-(4-amino-3-(furan-2-yl)-1H-pyrazolo[3,4-d]pyrimidin-1-yl)ethyl)-3-(3-fluorophenyl)-4H-chromen-4-one;

2-(1-(4-amino-3-(4-ethoxyphenyl)-1H-pyrazolo[3,4-d]pyrimidin-1-yl)ethyl)-3-(3-fluorophenyl)-4H-chromen-4-one;

2-(1-(4-amino-3-(3-chloro-4-methoxyphenyl)-1H-pyrazolo[3,4-d]pyrimidin-1-yl)ethyl)-3-(3-fluorophenyl)-4H-chromen-4-one;

2-(1-(4-amino-3-(3-fluoro-4-isopropoxyphenyl)-1H-pyrazolo[3,4-d]pyrimidin-1-yl)ethyl)-3-(3-fluorophenyl)-4H-chromen-4-one;

2-(1-(4-amino-3-(6-fluoropyridin-3-yl)-1H-pyrazolo[3,4-d]pyrimidin-1-yl)ethyl)-3-(3-fluorophenyl)-4H-chromen-4-one;

2-(1-(4-amino-3-(pyrimidin-5-yl)-1H-pyrazolo[3,4-d]pyrimidin-1-yl)ethyl)-3-(3-fluorophenyl)-4H-chromen-4-one;

2-(1-(4-amino-3-(3-(methoxymethyl)phenyl)-1H-pyrazolo[3,4-d]pyrimidin-1-yl)ethyl)-3-(3-fluorophenyl)-4H-chromen-4-one;

2-(1-(4-amino-3-(6-hydroxynaphthalen-2-yl)-1H-pyrazolo[3,4-d]pyrimidin-1-yl)ethyl)-3-(3-fluorophenyl)-4H-chromen-4-one;

2-(1-(4-amino-3-(3-isopropoxyphenyl)-1H-pyrazolo[3,4-d]pyrimidin-1-yl)ethyl)-3-(3-fluorophenyl)-4H-chromen-4-one;

2-(1-(4-amino-3-(1-methyl-1H-pyrazol-4-yl)-1H-pyrazolo[3,4-d]pyrimidin-1-yl)ethyl)-3-(3-fluorophenyl)-4H-chromen-4-one;

6-Fluoro-3-(3-fluorophenyl)-2-(1-(4-methoxyphenylamino)ethyl)-4H-chromen-4-one;

2-(1-(4-Chloro-7H-pyrrolo[2,3-d]pyrimidin-7-yl)ethyl)-3-(3-fluorophenyl)-4H-chromen-4-one;

2-(1-(4-Chloro-1H-pyrazolo[3,4-b]pyridin-1-yl)ethyl)-3-(3-fluorophenyl)-4H-chromen-4-one;

2-(1-(4-Chloro-1H-pyrazolo[3,4-d]pyrimidin-1-yl)ethyl)-3-(3-fluorophenyl)-4H-chromen-4-one;

2-(1-(4-Chloro-5H-pyrrolo[3,2-d]pyrimidin-5-yl)ethyl)-3-(3-fluorophenyl)-4H-chromen-4-one;

2-(1-(4-amino-3-(1,3-dimethyl-1H-indazol-6-yl)-1H-pyrazolo[3,4-d]pyrimidin-1-yl)ethyl)-3-(3-fluorophenyl)-4H-chromen-4-one;

2-(1-(4-amino-3-(2,3-dimethyl-2H-indazol-6-yl)-1H-pyrazolo[3,4-d]pyrimidin-1-yl)ethyl)-3-(3-fluorophenyl)-4H-chromen-4-one;

2-(1-(4-amino-3-(6-methoxynaphthalen-2-yl)-1H-pyrazolo[3,4-d]pyrimidin-1-yl)ethyl)-3-(3-fluorophenyl)-4H-chromen-4-one;

2-(1-(4-amino-3-(benzo[b]thiophen-3-yl)-1H-pyrazolo[3,4-d]pyrimidin-1-yl)ethyl)-3-(3-fluorophenyl)-4H-chromen-4-one;

2-(1-(4-amino-3-(2,4-dimethoxypyrimidin-5-yl)-1H-pyrazolo[3,4-d]pyrimidin-1-yl)ethyl)-3-(3-fluorophenyl)-4H-chromen-4-one;

2-(1-(4-amino-3-(6-ethoxynaphthalen-2-yl)-1H-pyrazolo[3,4-d]pyrimidin-1-yl)ethyl)-3-(3-fluorophenyl)-4H-chromen-4-one;

3-(4-amino-1-(1-(3-(3-fluorophenyl)-4-oxo-4H-chromen-2-yl)ethyl)-1H-pyrazolo[3,4-d]pyrimidin-3-yl)-N-cyclopropylbenzamide;

2-(1-(4-amino-3-(3-(morpholine-4-carbonyl)phenyl)-1H-pyrazolo[3,4-d]pyrimidin-1-yl)ethyl)-3-(3-fluorophenyl)-4H-chromen-4-one;

2-(1-(4-amino-3-(3-(difluoromethoxy)phenyl)-1H-pyrazolo[3,4-d]pyrimidin-1-yl)ethyl)-3-(3-fluorophenyl)-4H-chromen-4-one;

5-(4-amino-1-(1-(3-(3-fluorophenyl)-4-oxo-4H-chromen-2-yl)ethyl)-1H-pyrazolo[3,4-d]pyrimidin-3-yl)furan-2-carbaldehyde;

(S)-2-(1-(4-amino-3-(3-fluoro-4-isopropoxyphenyl)-1H-pyrazolo[3,4-d]pyrimidin-1-yl)ethyl)-3-(3-fluorophenyl)-4H-chromen-4-one;

(R)-2-(1-(4-amino-3-(3-fluoro-4-isopropoxyphenyl)-1H-pyrazolo[3,4-d]pyrimidin-1-yl)ethyl)-3-(3-fluorophenyl)-4H-chromen-4-one;

2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;

(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;

(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;

2-(6-Amino-9H-purin-9-yl)methyl)-3-(3-fluorophenyl)-5-methoxy-4H-chromen-4-one;

2-((4-Amino-3-(3-fluoro-4-isopropoxyphenyl)-1H-pyrazolo[3,4-d]pyrimidin-1-yl)methyl)-3-(3-fluorophenyl)-5-methoxy-4H-chromen-4-one;

2-((4-amino-3-(3-fluoro-4-isopropoxyphenyl)-1H-pyrazolo[3,4-d]pyrimidin-1-yl)methyl)-5-fluoro-3-(3-fluorophenyl)-4H-chromen-4-one;

2-((4-amino-3-(3-fluoro-5-methoxyphenyl)-1H-pyrazolo[3,4-d]pyrimidin-1-yl)methyl)-5-fluoro-3-(3-fluorophenyl)-4H-chromen-4-one;

2-((4-amino-3-(3-fluoro-5-hydroxyphenyl)-1H-pyrazolo[3,4-d]pyrimidin-1-yl)methyl)-5-fluoro-3-(3-fluorophenyl)-4H-chromen-4-one;

2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one;

(+)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one;

(−)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one;

2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one;

(+)-2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one;

(−)-2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one;

2-(1-(4-amino-3-(1H-pyrazol-4-yl)-1H-pyrazolo[3,4-d]pyrimidin-1-yl)ethyl)-5-fluoro-3-(3-fluorophenyl)-4H-chromen-4-one;

2-(1-(6-amino-9H-purin-9-yl)ethyl)-5-fluoro-3-(3-fluorophenyl)-4H-chromen-4-one;

2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one;

2-(1-(4-amino-3-(3-fluoro-4-isopropoxyphenyl)-1H-pyrazolo[3,4-d]pyrimidin-1-yl)ethyl)-5-fluoro-3-phenyl-4H-chromen-4-one;

2-(1-(4-amino-3-(benzofuran-2-yl)-1H-pyrazolo[3,4-d]pyrimidin-1-yl)ethyl)-5-fluoro-3-(3-fluorophenyl)-4H-chromen-4-one;

2-(1-(9H-purin-6-ylamino)ethyl)-5-fluoro-3-(3-fluorophenyl)-4H-chromen-4-one;

2-(1-(4-amino-1H-pyrazolo[3,4-d]pyrimidin-1-yl)ethyl)-5-fluoro-3-(3-fluorophenyl)-4H-chromen-4-one;

(+)-2-(1-(4-amino-1H-pyrazolo[3,4-d]pyrimidin-1-yl)ethyl)-5-fluoro-3-(3-fluorophenyl)-4H-chromen-4-one;

(−)-2-(1-(4-amino-1H-pyrazolo[3,4-d]pyrimidin-1-yl)ethyl)-5-fluoro-3-(3-fluorophenyl)-4H-chromen-4-one;

2-(1-(4-amino-3-(4-(difluoromethoxy)-3-fluorophenyl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-isopropoxyphenyl)-1H-pyrazolo[3,4-d]pyrimidin-1-yl)ethyl)-5-fluoro-3-(1H-pyrazol-4-yl)-4H-chromen-4-one;

2-(1-(4-amino-3-(3-fluoro-4-(tetrahydro-2H-pyran-4-yloxy)phenyl)-1H-pyrazolo[3,4-d]pyrimidin-1-yl)ethyl)-5-fluoro-3-(3-fluorophenyl)-4H-chromen-4-one;

2-(1-(4-amino-3-(3-isopropyl-1H-indazol-6-yl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-(piperidin-4-yloxy)phenyl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-(2-hydroxyethylamino)phenyl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-(isopropylamino)phenyl)-1H-pyrazolo[3,4-d]pyrimidin-1-yl)ethyl)-5-fluoro-3-(3-fluorophenyl)-4H-chromen-4-one;

2-(1-(4-amino-3-(4-(dimethylamino)-3-fluorophenyl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one;

2-(1-(4-amino-3-(2-methyl-1H-benzo[d]imidazol-5-yl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-(4-methylpiperazin-1-yl)phenyl)-1H-pyrazolo[3,4-d]pyrimidin-1-yl)ethyl)-5-fluoro-3-(3-fluorophenyl)-4H-chromen-4-one;

2-(1-(4-(dimethylamino)-1H-pyrazolo[3,4-d]pyrimidin-1-yl)ethyl)-5-fluoro-3-(3-fluorophenyl)-4H-chromen-4-one;

2-(1-(4-amino-1H-pyrazolo[3,4-d]pyrimidin-1-yl)ethyl)-5-fluoro-3-phenyl-4H-chromen-4-one;

2-(1-(4-amino-1H-pyrazolo[3,4-d]pyrimidin-1-yl)ethyl)-5-fluoro-3-(4-fluorophenyl)-4H-chromen-4-one;

2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one;

2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one;

2-(1-(4-amino-3-methyl-1H-pyrazolo[3,4-d]pyrimidin-1-yl)ethyl)-5-fluoro-3-(3-fluorophenyl)-4H-chromen-4-one;

2-(1-(4-amino-3-ethyl-1H-pyrazolo[3,4-d]pyrimidin-1-yl)ethyl)-5-fluoro-3-(3-fluorophenyl)-4H-chromen-4-one;

2-(1-(4-amino-3-isopropyl-1H-pyrazolo[3,4-d]pyrimidin-1-yl)ethyl)-5-fluoro-3-(3-fluorophenyl)-4H-chromen-4-one;

2-(1-(4-amino-3-(benzo[b]thiophen-2-yl)-1H-pyrazolo[3,4-d]pyrimidin-1-yl)ethyl)-5-fluoro-3-(3-fluorophenyl)-4H-chromen-4-one;

2-(1-(4-amino-3-morpholino-1H-pyrazolo[3,4-d]pyrimidin-1-yl)ethyl)-5-fluoro-3-(3-fluorophenyl)-4H-chromen-4-one;

2-(1-(4-amino-3-(dimethylamino)-1H-pyrazolo[3,4-d]pyrimidin-1-yl)ethyl)-5-fluoro-3-(3-fluorophenyl)-4H-chromen-4-one;

2-(1-(4-amino-3-(piperidin-1-yl)-1H-pyrazolo[3,4-d]pyrimidin-1-yl)ethyl)-5-fluoro-3-(3-fluorophenyl)-4H-chromen-4-one;

2-(1-(4-amino-3-(6-isopropoxypyridin-3-yl)-1H-pyrazolo[3,4-d]pyrimidin-1-yl)ethyl)-5-fluoro-3-(3-fluorophenyl)-4H-chromen-4-one;

2-(1-(4-amino-3-(methylthio)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one 4-methylbenzenesulfonate;

2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one 4-methylbenzenesulfonate;

2-(1-(4-amino-3-(4-(1-benzhydrylazetidin-3-yloxy)-3-fluorophenyl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-(trifluoromethoxy)phenyl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-(oxetan-3-yloxy)phenyl)-1H-pyrazolo[3,4-d]pyrimidin-1-yl)ethyl)-5-fluoro-3-(3-fluorophenyl)-4H-chromen-4-one;

2-(1-(4-amino-3-(pyrrolidin-1-yl)-1H-pyrazolo[3,4-d]pyrimidin-1-yl)ethyl)-5-fluoro-3-(3-fluorophenyl)-4H-chromen-4-one;

N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)phenyl)isobutyramide;

2-(1-(4-amino-3-(4-isobutylphenyl)-1H-pyrazolo[3,4-d]pyrimidin-1-yl)ethyl)-5-fluoro-3-(3-fluorophenyl)-4H-chromen-4-one;

2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one;

2-(1-(4-amino-3-(4-(5,6-dihydro-4H-1,3-oxazin-2-yl)phenyl)-1H-pyrazolo[3,4-d]pyrimidin-1-yl)ethyl)-5-fluoro-3-(3-fluorophenyl)-4H-chromen-4-one;

4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-methylbenzenesulfonamide;

4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluoro-N-isopropylbenzamide;

2-(1-(4-amino-3-(4-(5-(methylamino)-1,3,4-thiadiazol-2-yl)phenyl)-1H-pyrazolo[3,4-d]pyrimidin-1-yl)ethyl)-5-fluoro-3-(3-fluorophenyl)-4H-chromen-4-one;

N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)benzyl)methanesulfonamide;

4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-isopropylbenzenesulfonamide;

4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-cyclopropylbenzenesulfonamide;

2-(1-(4-amino-3-(2-isopropoxypyrimidin-5-yl)-1H-pyrazolo[3,4-d]pyrimidin-1-yl)ethyl)-5-fluoro-3-(3-fluorophenyl)-4H-chromen-4-one;

(R)/(S)-2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one;

4-(4-amino-1-(1-(5-fluoro-3-(3-fluorophenyl)-4-oxo-4H-chromen-2-yl)ethyl)-1H-pyrazolo[3,4-d]pyrimidin-3-yl)benzenesulfonamide;

methyl 4-(4-amino-1-(1-(5-fluoro-3-(3-fluorophenyl)-4-oxo-4H-chromen-2-yl)ethyl)-1H-pyrazolo[3,4-d]pyrimidin-3-yl)thiophene-2-carboxylate;

2-(1-(4-amino-3-(5-methylthiophen-2-yl)-1H-pyrazolo[3,4-d]pyrimidin-1-yl)ethyl)-5-fluoro-3-(3-fluorophenyl)-4H-chromen-4-one;

2-(1-(4-amino-3-(1H-pyrrolo[2,3-b]pyridin-5-yl)-1H-pyrazolo[3,4-d]pyrimidin-1-yl)ethyl)-5-fluoro-3-(3-fluorophenyl)-4H-chromen-4-one;

methyl 4-(4-amino-1-(1-(5-fluoro-3-(3-fluorophenyl)-4-oxo-4H-chromen-2-yl)ethyl)-1H-pyrazolo[3,4-d]pyrimidin-3-yl)-3-fluorobenzoate;

2-(1-(9H-purin-6-ylamino)propyl)-5-fluoro-3-phenyl-4H-chromen-4-one;

2-(1-(4-amino-3-(3-hydroxyprop-1-ynyl)-1H-pyrazolo[3,4-d]pyrimidin-1-yl)ethyl)-5-fluoro-3-(3-fluorophenyl)-4H-chromen-4-one;

(S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one 4-methylbenzenesulfonate;

(+)-2-(1-(9H-purin-6-ylamino)ethyl)-5-fluoro-3-(3-fluorophenyl)-4H-chromen-4-one 2-(1-(9H-purin-6-ylamino)ethyl)-5-fluoro-3-(3-fluorophenyl)-4H-chromen-4-one;

(R)/(S)-2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one;

2-(1-(4-amino-3-(4-methoxy-3,5-dimethylphenyl)-1H-pyrazolo[3,4-d]pyrimidin-1-yl)ethyl)-5-fluoro-3-(3-fluorophenyl)-4H-chromen-4-one;

2-(1-(4-amino-3-(4-(methoxymethyl)phenyl)-1H-pyrazolo[3,4-d]pyrimidin-1-yl)ethyl)-5-fluoro-3-(3-fluorophenyl)-4H-chromen-4-one;

2-(1-(4-amino-3-(imidazo[1,2-a]pyridin-6-yl)-1H-pyrazolo[3,4-d]pyrimidin-1-yl)ethyl)-5-fluoro-3-(3-fluorophenyl)-4H-chromen-4-one;

tert-butyl(5-(4-amino-1-(1-(5-fluoro-3-(3-fluorophenyl)-4-oxo-4H-chromen-2-yl)ethyl)-1H-pyrazolo[3,4-d]pyrimidin-3-yl)furan-2-yl)methylcarbamate;

2-(1-(4-amino-3-(2,4-dimethylthiazol-5-yl)-1H-pyrazolo[3,4-d]pyrimidin-1-yl)ethyl)-5-fluoro-3-(3-fluorophenyl)-4H-chromen-4-one;

2-(1-(4-amino-3-(5-(morpholinomethyl)thiophen-2-yl)-1H-pyrazolo[3,4-d]pyrimidin-1-yl)ethyl)-5-fluoro-3-(3-fluorophenyl)-4H-chromen-4-one;

2-(1-(4-amino-3-(4-(5-amino-1,3,4-thiadiazol-2-yl)phenyl)-1H-pyrazolo[3,4-d]pyrimidin-1-yl)ethyl)-5-fluoro-3-(3-fluorophenyl)-4H-chromen-4-one;

(−)-2-(1-(9H-purin-6-ylamino)ethyl)-5-fluoro-3-(3-fluorophenyl)-4H-chromen-4-one;

2-(1-(4-amino-3-(1,3-dimethyl-1H-indazol-6-yl)-1H-pyrazolo[3,4-d]pyrimidin-1-yl)ethyl)-5-fluoro-3-(3-fluorophenyl)-4H-chromen-4-one;

2-(1-(4-amino-3-(2,3-dimethyl-2H-indazol-6-yl)-1H-pyrazolo[3,4-d]pyrimidin-1-yl)ethyl)-5-fluoro-3-(3-fluorophenyl)-4H-chromen-4-one;

N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluorophenyl)isobutyramide;

N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluorophenyl)acetamide;

2-(1-(4-(dimethylamino)-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one;

5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one;

5-fluoro-2-(1-(3-(3-fluoro-4-isopropoxyphenyl)-4-morpholino-1H-pyrazolo[3,4-d]pyrimidin-1-yl)ethyl)-3-(3-fluorophenyl)-4H-chromen-4-one;

N-(2-fluoro-4-(1-(1-(5-fluoro-3-(4-fluorophenyl)-4-oxo-4H-chromen-2-yl)ethyl)-4-morpholino-1H-pyrazolo[3,4-d]pyrimidin-3-yl)phenyl)isobutyramide;

N-(2-fluoro-4-(1-(1-(5-fluoro-3-(3-fluorophenyl)-4-oxo-4H-chromen-2-yl)ethyl)-4-morpholino-1H-pyrazolo[3,4-d]pyrimidin-3-yl)phenyl)isobutyramide;

(S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one sulphate;

(S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one;

(S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one camphorsulphonate;

2-(1-(4-amino-3-(4-(difluoromethoxy)-3-fluorophenyl)-1H-pyrazolo[3,4-d]pyrimidin-1-yl)ethyl)-5-fluoro-3-(1H-pyrazol-4-yl)-4H-chromen-4-one;

2-(1-(4-amino-3-(3-fluoro-4-morpholinophenyl)-1H-pyrazolo[3,4-d]pyrimidin-1-yl)ethyl)-5-fluoro-3-phenyl-4H-chromen-4-one;

2-(1-(4-amino-3-(3-fluoro-4-morpholinophenyl)-1H-pyrazolo[3,4-d]pyrimidin-1-yl)ethyl)-5-fluoro-3-(4-fluorophenyl)-4H-chromen-4-one;

(S)-2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one;

(R)-2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one;

(S)-2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one;

(R)-2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one;

2-(1-(4-(dimethylamino)-3-(3-fluoro-4-morpholinophenyl)-1H-pyrazolo[3,4-d]pyrimidin-1-yl)ethyl)-5-fluoro-3-(3-fluorophenyl)-4H-chromen-4-one;

5-fluoro-2-(1-(3-(3-fluoro-4-morpholinophenyl)-4-(methylamino)-1H-pyrazolo[3,4-d]pyrimidin-1-yl)ethyl)-3-(3-fluorophenyl)-4H-chromen-4-one;

(S)-2-(1-(4-amino-3-(3-fluoro-4-isopropoxyphenyl)-1H-pyrazolo[3,4-d]pyrimidin-1-yl)ethyl)-5-fluoro-3-phenyl-4H-chromen-4-one;

(R)-2-(1-(4-amino-3-(3-fluoro-4-isopropoxyphenyl)-1H-pyrazolo[3,4-d]pyrimidin-1-yl)ethyl)-5-fluoro-3-phenyl-4H-chromen-4-one;

(S)-2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one;

(R)-2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one;

(+)-5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one;

(−)-5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one;

2-(1-(6-amino-2-fluoro-9H-purin-9-yl)ethyl)-5-fluoro-3-(3-fluorophenyl)-4H-chromen-4-one;

2-(1-(6-amino-2-fluoro-9H-purin-9-yl)ethyl)-5-fluoro-3-(4-fluorophenyl)-4H-chromen-4-one;

5-fluoro-3-(4-fluorophenyl)-2-(1-(6-morpholino-9H-purin-9-yl)ethyl)-4H-chromen-4-one;

5-fluoro-3-(4-fluorophenyl)-2-(1-(6-(4-methylpiperazin-1-yl)-9H-purin-9-yl)ethyl)-4H-chromen-4-one;

2-(1-(6-(dimethylamino)-9H-purin-9-yl)ethyl)-5-fluoro-3-(3-fluorophenyl)-4H-chromen-4-one;

2-(1-(6-(dimethylamino)-9H-purin-9-yl)ethyl)-5-fluoro-3-(3-fluorophenyl)-4H-chromen-4-one;

5-fluoro-3-(3-fluorophenyl)-2-(1-(3-(3-methyl-1H-indazol-6-yl)-4-morpholino-1H-pyrazolo[3,4-d]pyrimidin-1-yl)ethyl)-4H-chromen-4-one;

2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one;

(+)-2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one;

(−)-2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one;

(S)/(R)-5-fluoro-2-(1-(3-(3-fluoro-4-isopropoxyphenyl)-4-morpholino-1H-pyrazolo[3,4-d]pyrimidin-1-yl)ethyl)-3-(3-fluorophenyl)-4H-chromen-4-one;

2-(1-(4-amino-3-(3-chloro-4-isopropoxyphenyl)-1H-pyrazolo[3,4-d]pyrimidin-1-yl)ethyl)-5-fluoro-3-(3-fluorophenyl)-4H-chromen-4-one;

2-(1-(4-amino-3-(2-methylbenzo[d]oxazol-6-yl)-1H-pyrazolo[3,4-d]pyrimidin-1-yl)ethyl)-5-fluoro-3-(3-fluorophenyl)-4H-chromen-4-one;

5-fluoro-3-(3-fluorophenyl)-2-(1-(6-morpholino-9H-purin-9-yl)ethyl)-4H-chromen-4-one;

2-(1-(4-amino-3-(3-fluoro-4-isopropoxyphenyl)-1H-pyrazolo[3,4-d]pyrimidin-1-yl)ethyl)-3-(3-fluorophenyl)-5-morpholino-4H-chromen-4-one;

2-(1-(4-amino-3-(3-fluoro-4-isopropoxyphenyl)-1H-pyrazolo[3,4-d]pyrimidin-1-yl)ethyl)-5-morpholino-3-phenyl-4H-chromen-4-one;

6-(4-amino-1-(1-(5-fluoro-3-(3-fluorophenyl)-4-oxo-4H-chromen-2-yl)ethyl)-1H-pyrazolo[3,4-d]pyrimidin-3-yl)isoindolin-1-one;

5-(4-amino-1-(1-(5-fluoro-3-(3-fluorophenyl)-4-oxo-4H-chromen-2-yl)ethyl)-1H-pyrazolo[3,4-d]pyrimidin-3-yl)isoindolin-1-one;

2-(1-(3-(4-acetyl-3-fluorophenyl)-4-amino-1H-pyrazolo[3,4-d]pyrimidin-1-yl)ethyl)-5-fluoro-3-(3-fluorophenyl)-4H-chromen-4-one;

5-fluoro-3-(3-fluorophenyl)-2-(1-(6-(4-methylpiperazin-1-yl)-9H-purin-9-yl)ethyl)-4H-chromen-4-one;

(S)-2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one;

(R)-2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one;

N-(3-(4-amino-1-(1-(5-fluoro-3-(3-fluorophenyl)-4-oxo-4H-chromen-2-yl)ethyl)-1H-pyrazolo[3,4-d]pyrimidin-3-yl)phenyl)methanesulfonamide;

(S)-2-(1-(6-(dimethylamino)-9H-purin-9-yl)ethyl)-5-fluoro-3-(3-fluorophenyl)-4H-chromen-4-one;

(R)-2-(1-(6-(dimethylamino)-9H-purin-9-yl)ethyl)-5-fluoro-3-(3-fluorophenyl)-4H-chromen-4-one;

2-(1-(9H-purin-6-ylamino)ethyl)-5-fluoro-3-(2-fluorophenyl)-4H-chromen-4-one;

2-(1-(4-amino-3-(4-ethoxy-3-(trifluoromethyl)phenyl)-4H-pyrazolo[3,4-d]pyrimidin-1-yl)ethyl)-5-fluoro-3-(3-fluorophenyl)-4H-chromen-4-one;

2-(1-(4-amino-3-(3-fluoro-4-isopropoxyphenyl)-1H-pyrazolo[3,4-d]pyrimidin-1-yl)propyl)-5-fluoro-3-(3-fluorophenyl)-4H-chromen-4-one;

(S)-5-fluoro-3-(3-fluorophenyl)-2-(1-(2-methoxy-9H-purin-6-ylamino)ethyl)-4H-chromen-4-one;

(R)-5-fluoro-3-(3-fluorophenyl)-2-(1-(2-methoxy-9H-purin-6-ylamino)ethyl)-4H-chromen-4-one;

(S)/(R)-5-fluoro-2-(1-(2-fluoro-9H-purin-6-ylamino) ethyl)-3-(3-fluoro phenyl)-4H-chromen-4-one;

(S)/(R)-2-(1-(4-amino-3-(3-fluoro-4-isopropoxyphenyl)-1H-pyrazolo[3,4-d]pyrimidin-1-yl)ethyl)-5-methyl-3-phenyl-4H-chromen-4-one;

2-(1-(9H-purin-6-ylamino)ethyl)-5-fluoro-3-o-tolyl-4H-chromen-4-one; and pharmaceutically acceptable salts thereof.

In another preferred embodiment, the compound of formula (I) is a PI3K Delta inhibitor selected from 2-((6-amino-9H-purin-9-yl)methyl)-5-methyl-3-o-tolylquinazolin-4(3H)-one (IC87114);

(S)-2-(1-((9H-purin-6-yl)amino)propyl)-5-fluoro-3-phenylquinazolin-4(3H)-one (CAL-101, Idelalisib);

INCB040093;

AMG 319;

(S)-2-(1-(9H-purin-6-ylamino)ethyl)-6-fluoro-3-(3-fluorophenyl)-4H-chromen-4-one (Compound C);

(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and pharmaceutically acceptable salts thereof.

In a further preferred embodiment, the compound of formula (I) is a dual PI3K Delta and Gamma inhibitor selected from (S)-3-(1-((9H-purin-6-yl)amino)ethyl)-8-chloro-2-phenylisoquinolin-1(2H)-one (IPI-145);

(+)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one (Compound A1);

(−)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one; and pharmaceutically acceptable salts thereof.

In a preferred embodiment, the PDE-4 inhibitor is apremilimast or roflumilast.

Yet another embodiment is a kit for treating an autoimmune, respiratory or inflammatory disease or condition, the kit comprising:

(i) a PI3K Delta or PI3K Delta and Gamma inhibitor, and (ii) a PDE4 inhibitor, either in a single pharmaceutical composition or in separate pharmaceutical compositions, (ii) optionally, instructions for treating the autoimmune, respiratory or inflammatory disease or condition with the PI3K Delta or PI3K Delta and Gamma inhibitor, and PDE4 inhibitor, and (iii) optionally, a container for placing the pharmaceutical composition or pharmaceutical compositions.

DETAILED DESCRIPTION OF THE INVENTION

Definitions

Figure 1:
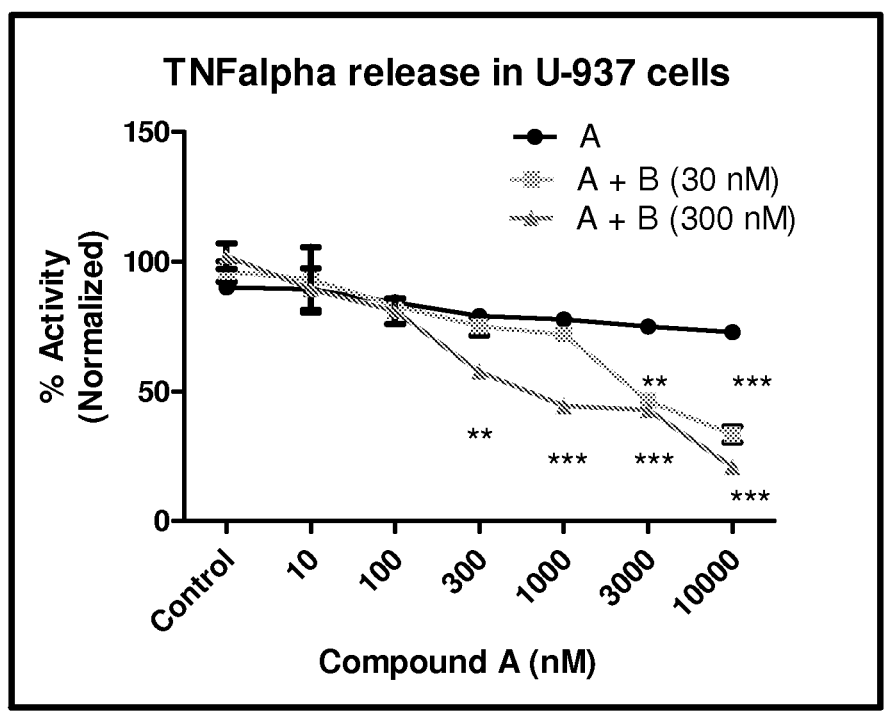
FIG. 1 depicts the effect of Compound A and its combination with Compound B at 30 and 300 nM on inhibition of TNFα release from U-937 cells. $p<0.01$ and *$p<0.001$ (versus Compound A).

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout: PI3-K=Phosphoinositide 3-kinase; PI=phosphatidylinositol; and MeI=Methyl Iodide.

Abbreviations used herein have their conventional meaning within the chemical and biological arts, unless otherwise indicated.

The terms "substituted or unsubstituted", "alkyl", "alkoxy", "alkenyl", "alkynyl", "aryl", "arylalkyl", "cycloalkyl", "cycloalkylalkyl", "cycloalkenylalkyl", "cycloalkenyl", "heteroaryl", "heteroarylalkyl", "heterocyclic ring" (or heterocyclyl), and "heterocyclylalkyl" are as defined in International Patent Application Nos. PCT/

IB2010/002804 and PCT/US2012/36594. Suitable pharmaceutically acceptable salts of the PI3K inhibitors described herein include those described in International Patent Application Nos. PCT/IB2010/002804 and PCT/US2012/36594.

The term "effective amount" or "therapeutically effective amount" refers to that amount of a compound or combination of compounds described herein that is sufficient to effect the intended application including, but not limited to, disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, the terms "treatment" and "treating" refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" refers to an animal, such as a mammal, for example a human. The methods described herein can be useful in both human therapeutics and veterinary applications. In some embodiments, the patient is a mammal, and in some embodiments, the patient is human. For veterinary purposes, the term "subject" and "patient" include, but are not limited to, farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

The term "selective inhibition" or "selectively inhibit" as applied to a biologically active agent refers to the agent's ability to selectively reduce the target signaling activity as compared to off-target signaling activity, via direct or indirect interaction with the target.

As used herein, the term "PI3-kinase δ selective inhibitor" generally refers to a compound that inhibits the activity of the PI3-kinase δ isozyme more effectively than other isozymes of the PI3K family (alpha, beta, and gamma). For instance, the PI3-kinase δ selective inhibitor may refer to a compound that exhibits a 50% inhibitory concentration (IC50) with respect to the delta type I PI3-kinase that is at least 10-fold, at least 20-fold, at least 50-fold, at least 100-fold, or lower, than the inhibitor's IC50 with respect to the rest of the other type I PI3-kinases (i.e., alpha, beta, and gamma).

As used herein, the term "Dual PI3-kinase Delta (δ) and Gamma (γ) inhibitor" generally refers to a compound that inhibits the activity of both the PI3-kinase δ and γ isozymes more effectively than other isozymes of the PI3K family. A PI3-kinase δ and γ dual inhibitor compound is therefore more selective for PI3-kinase δ and γ than conventional PI3K inhibitors such as wortmannin and LY294002, which are "non-selective PI3K inhibitors."

For instance, the Dual PI3-kinase δ and γ selective inhibitor may refer to a compound that exhibits a 50% inhibitory concentration (IC50) with respect to the delta and gamma type I PI3-kinase that is at least 10-fold, at least 20-fold, at least 50-fold, at least 100-fold, or lower, than the inhibitor's IC50 with respect to the rest of the other type I PI3-kinases (i.e., alpha, and beta).

The therapeutic methods of the invention include methods for the treatment of conditions associated with an inflammatory response. An "Inflammatory response" is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis. Inflammatory responses may result from infection with pathogenic organisms and viruses, noninfectious means such as trauma or reperfusion following myocardial infarction or stroke, immune responses to foreign antigens, and autoimmune diseases. Inflammatory responses amenable to treatment with the methods and compounds according to the invention encompass conditions associated with reactions of the specific defense system as well as conditions associated with reactions of the non-specific defense system.

The therapeutic methods of the invention include methods for the treatment of conditions associated with inflammatory cell activation. "Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including, but not limited to, monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Autoimmune disease" as used herein refers to any group of disorders in which tissue injury is associated with humoral or cell-mediated responses to the body's own constituents.

An "allergic" disease generally refers to any symptoms, tissue damage, or loss of tissue function resulting from allergy An "arthritic" disease generally refers to any disease that is characterized by inflammatory lesions of the joints attributable to a variety of etiologies.

"Dermatitis" generally refers to any of a large family of diseases of the skin that are characterized by inflammation of the skin attributable to a variety of etiologies.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "pharmaceutically acceptable salts" as used herein includes salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; salts of chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, omithine, lysine, arginine, and serine; quaternary ammonium salts of the compounds of invention with alkyl halides, alkyl sulphates such as MeI and $(Me)_2SO_4$; salts of non-natural amino acids such as D-isomers or substituted amino acids; salts of guanidine; and salts of substituted guanidine wherein the substituents are selected from nitro, amino, alkyl, alkenyl, alkynyl, ammonium or substituted ammonium salts and aluminum salts. Salts may include acid addition salts where appropriate which are sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

PI3K Delta and Dual PI3K Delta and Gamma Inhibitors

Examples of PI3-kinase δselective inhibitors and dual PI3-kinase delta (δ) and gamma (γ) inhibitors that may be used in the compositions and methods described herein include, but are not limited to, CAL-101 (idelalisib), IPI-145 (duvelisib) and the compounds disclosed in International Publication No. WO 2012/151525, U.S. Patent Publication Nos. 2011/0118257 and 2012/0289496, International Patent Application Nos. PCT/IB2010/002804, filed Nov. 3, 2010, PCT/US2012/36594, filed May 4, 2012, PCT/US2013/055434, filed Jul. 2, 2013 and U.S. patent application Ser. No. 13/933,856, filed Jul. 2, 2013. Additional non limiting examples are also disclosed in International Publication Nos. WO 2001/081346, WO 2003/035075, WO 2005/113554, WO 200/113556, WO 2006/024666, WO 2008/118454, WO 2008/118455, WO 2009/010530, WO 2009/064802, WO 2009/088986, WO 2009/088990, WO 2009/147189, WO 2010/005558, WO 2010/051042, WO 2010/051043, WO 2010/056320, WO 2010/057048, WO 2010/092015, WO 2010/092962, WO 2010/096389, WO 2010/102958, WO 2010/110685, WO 2010/110686, WO 2010/111432, WO 2010/123931, WO 2010/135014, WO 2010/136491, WO 2010/138589, WO 2010/144513, WO 2010/151737, WO 2010/151740, WO 2010/151791, WO 2011/005119, WO 2011/008302, WO 2011/008487, WO 2011/011550, WO 2011/012883, WO 2011/021038, WO 2011/022439, WO 2011/041399, WO 2011/041634, WO 2011/048111, WO 2011/048936, WO 2011/055215, WO 2011/075268, WO 2011/075630, WO 2011/075643, WO 2011/101429, WO 2011/123751, WO 2011/130342, WO 2011/156759, WO 2011/163195, WO 2012/003262, WO 2012/003264, WO 2012/003271, WO 2012/003274, WO 2012/003278, WO 2012/003283, WO 2012/004299, WO 2012/007493, WO 2012/0135009, WO 2012/020762, WO 2012/021696, WO 2012/032067, WO 2012/037204, WO 2012/037226, WO 2012/040634, WO 2012/044641, WO 2012/052753, WO 2012/055846, WO 2012/061696, WO 2012/064973, WO 2012/068343, WO 2012/087784, WO 2012/087881, WO 2012/097000, WO 2012/107465, WO 2012/116237, WO 2012/121953, WO 2012/125510, WO 2012/125629, WO 2012/126901, WO 2012/135160, WO 2012/135166, WO 2012/135175, WO 2012/140419, WO 2012/146666, WO 2012/146667, WO 2012/148548, WO 2012/151525, US 2012/0220575, US 2012/0238587, WO 2013/012915, WO 2013/012918, WO 2013/032591, WO 2013/033569, WO 2013/052699, WO 2013/057711, WO 2013/067141, WO 2013/067306, WO 2013/071264, WO 2013/078441, WO 2013/082540, WO 2013/090725, WO 2013/116562, WO 2013/132270, WO 2013/134288, WO 2013/136075 and WO 2013/136076. Each of these publications describing PI3K inhibitors and their preparation are incorporated herein by reference.

PDE-4 Inhibitors

Suitable PDE-4 inhibitors for use in the compositions and methods described herein include, but are not limited to, enprofylline, theophylline, aminophylline, oxtriphylline, apremilast, roflumilast, ariflo (cilomilast), tofimilast, pumafentrine, lirimilast, arofylline, atizorame, oglemilastum, D-4418, Bay-198004, BY343, CP-325,366, D-4396 (Sch-351591), AWD-12-281 (GW-842470), NCS-613, CDP-840, D-4418, PD-168787, T-440, T-2585, V 1 1294A, CI-1018, CDC-801, CDC-3052, D-22888, YM-58997, Z-15370, N-(3,5-dichloro-1-oxo-pyridin-4-yl)-4-difluoromethoxy-3-cyclopropylmethoxybenzamide, (−)-p-[(4aR*, 10bS*)-9-ethoxy-1,2,3,4,4a,10b-hexahydro-8-methoxy-2-methyl-benzo[s][1,6]-naphthyridin-6-yl]-N,N-diiso-propylbenzamid(R)-(+)-1-(4-bromobenzyl)-4-[(3-cyclopentyloxy)-4-methoxy phenyl]-2-pyrrolidon, 3-(cyclopentyloxy-4-methoxyphenyl)-1-(4-N'-[N-2-cyano-S-methyl-isothio ureido]benzyl)-2-pyrrolidone, cis[4-cyano-4-(3-cyclopentyloxy-4-methoxy phenyl)cyclohexan-1-carboxylicacid], 2-carbomethoxy-4-cyano-4-(3-cyclopropylmethoxy-4-difluoromethoxy phenyl) cyclohexan-1-one, cis[4-cyano-4-(3-cyclopropylmethoxy-4-difluoromethoxy phenyl)cyclohexan-1-ol], (R)-(+)-ethyl [4-(3-cyclopentyloxy-4-methoxyphenyl) pyrrolidin-2-yliden]acetate, (S)-(−)-ethyl[4-(3-cyclopentyloxy-4-methoxyphenyl)pyrrolidin-2-yliden]acetate, 9 cyclopentyl-5,6-dihydro-7-ethyl-3-(2-thienyl)-9H-pyrazolo[3,4c]-1,2,4-triazolo[4,3a]pyridine and 9-cyclopentyl-5,6-dihydro-7-ethyl-3-(tert-butyl)-9H-pyrazolo[3,4c]-1,2,4-triazolo[4,3a] pyridine, optionally in racemic form, as enantiomers, diastereomers or as pharmacologically acceptable salts, solvates or hydrates or the compounds as disclosed in the WO 2012/016845 and WO 2012/016889.

In a preferred embodiment, the PDE4 inhibitor is selected from theophylline, aminophylline, oxtriphylline, roflumilast and apremilast. In a further preferred embodiment, the PDE4 inhibitor is roflumilast. In yet another embodiment, the PDE4 inhibitor is apremilast.

Pharmaceutical Compositions

In one aspect, the present invention provides a pharmaceutical composition comprising a PI3K Delta or dual PI3K Delta and Gamma dual inhibitor and a PDE4 inhibitor, and, optionally, one or more pharmaceutically acceptable carriers or excipients.

In one embodiment, the pharmaceutical composition includes a therapeutically effective amount of PI3K Delta or dual PI3K Delta and Gamma inhibitor and a therapeutically effective amount of PDE4 inhibitor. In another embodiment, the pharmaceutical composition includes a synergistic effective amount of (i) PI3K Delta or dual PI3K Delta and Gamma inhibitor and (ii) PDE4 inhibitor. For example, the pharmaceutical composition may include from about 0.1 µg to about 2 gm, preferably from about 1 µg to about 1000 mg, more preferably from about 10 µg to about 500 mg, such as from about 100 µg to about 100 mg, of the PI3K Delta or dual PI3K Delta and Gamma inhibitor, and from about 0.1 µg to about 500 mg, preferably from about 1 µg to about 100 mg, more preferably from about 10 µg to about 50 mg, such as from about 10 µg to about 10 mg of the PDE4 inhibitor.

The pharmaceutical composition may further include one or more additional active ingredients, such as those useful for the prevention and/or treatment of a respiratory disease, such as beta2-agonists (e.g., salbutamol, salmeterol, and vilanterol); corticosteroids (such as fluticasone propionate or furoate, flunisolide, mometasone furoate, rofleponide and ciclesonide); and anticholinergic or antimuscarinic agents (such as ipratropium bromide, oxytropium bromide, tiotropium bromide, and oxybutynin); and combinations thereof.

The pharmaceutical carriers and/or excipients may be selected from diluents, fillers, salts, disintegrants, binders, lubricants, glidants, wetting agents, controlled release matrices, colorants, flavourings, buffers, stabilizers, solubilizers, and combinations thereof.

The pharmaceutical compositions of the present invention can be administered alone or in combination with one or more additional active ingredients, such as those described above. The pharmaceutical compositions of the present invention can be administered together or in a sequential manner with one or more of the other active ingredients. Where desired, the pharmaceutical composition of the present invention and other active ingredients may be co-administered or both may be administered in a sequence to use them as a combination.

The compounds and pharmaceutical compositions of the present invention can be administered by any route that enables delivery of the compounds to the site of action, such as, but not limited to, orally, intranasally, topically (e.g., transdermally), intraduodenally, parenterally (including intravenously, intraarterially, intramuscularally, intravascularly, intraperitoneally or by injection or infusion), intradermally, by intramammary, intrathecally, intraocularly, retrobulbarly, intrapulmonary (e.g., aerosolized drugs) or subcutaneously (including depot administration for long term release e.g., embedded-under the-splenic capsule, brain, or in the cornea), sublingually, anally, rectally, vaginally, or by surgical implantation (e.g., embedded under the splenic capsule, brain, or in the cornea) or by inhalation.

The compositions can be administered in solid, semi-solid, liquid or gaseous form, or may be in dried powder, such as lyophilized form. The pharmaceutical compositions can be packaged in forms convenient for delivery, including, for example, solid dosage forms such as capsules, sachets, cachets, gelatins, papers, tablets, suppositories, pellets, pills, troches, and lozenges. The type of packaging will generally depend on the desired route of administration. Implantable sustained release formulations are also contemplated, as are transdermal formulations. In one preferred embodiment, the pharmaceutical composition is a solid oral dosage form, such as a tablet or capsule.

In another embodiment, the pharmaceutical composition is suitable for inhalation (e.g., by being aerosolized).

The present invention further relates to a pharmaceutical composition according to any embodiment described herein for use in the treatment of autoimmune, respiratory and/or inflammatory diseases and conditions.

Another embodiment of the present invention relates to a method of treating autoimmune respiratory and/or inflammatory diseases and conditions, comprising administering to a subject in need thereof a therapeutically effective amount of a pharmaceutical composition according to any of the embodiments described herein.

Another embodiment of the present invention relates to the use of a pharmaceutical composition according to any of the embodiments described herein for the manufacture of a medicament for treating autoimmune, respiratory and/or inflammatory diseases and conditions in a subject in need thereof.

In the pharmaceutical compositions according to any of the embodiments described herein, the PI3K Delta inhibitor may be in the form of a solvate, a hydrate or as salt with pharmacologically acceptable acid or base.

In the pharmaceutical compositions according to any of the embodiments described herein, the Dual PI3K Delta and Gamma inhibitor may be in the form of a solvate, a hydrate or as salt with pharmacologically acceptable acid or base.

In the pharmaceutical compositions according to any of the embodiments described herein, the PDE4 inhibitor may be may be in the form of a solvate, a hydrate or as salt with pharmacologically acceptable acid or base.

In one embodiment, the present invention relates to a pharmaceutical composition according to any of the embodiments described herein, wherein the PDE4 inhibitor is roflumilast.

Another particular embodiment of the present invention relates to pharmaceutical compositions according to any of the embodiments described herein, wherein the PDE4 inhibitor is aprelimilast.

Yet another particular embodiment of the present invention relates to pharmaceutical compositions according to any of the embodiments described herein, wherein the PDE4 inhibitor is theophylline.

Methods of Treatment

Another embodiment of the present invention is a method of treating an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, or a renal disease or disorder. The method includes administering an effective amount of a PI3K Delta or dual PI3K Delta and Gamma dual inhibitor and a PDE4 inhibitor.

The PI3K Delta or dual PI3K Delta and Gamma dual inhibitor and PDE4 inhibitor (and optionally other active ingredients) can be incorporated in a single pharmaceutical composition and administered, or alternatively, can be administered in separate pharmaceutical compositions, which can be administered at the same time or at different times.

The amount of each compound to be administered depends on the subject (such as a mammal or human in particular) being treated, the severity of the disorder or condition, the rate of administration, the disposition of the compound and the discretion of the prescribing physician. In one embodiment, the effective dosage for the PI3K Delta or PI3K Delta and Gamma dual inhibitor is from about 0.001 to about 100 mg per kg body weight per day, for example, from about 1 to about 35 mg/kg/day, in single or divided doses. For a 70 kg human, this would amount to about 0.05 to 7 g/day, preferably about 0.05 to about 2.5 g/day. In one embodiment, the effective dosage for the PDE4 inhibitor is from about 0.001 to about 100 mg per kg body weight per day, for example, from about 0.1 to about 100 mcg/kg/day, in single or divided doses (e.g., from about 7 to about 7000 mcg/day or from about 10 to about 1000 mcg/day). An effective amount of the PI3K Delta or PI3K Delta and Gamma dual inhibitor and/or PDE4 inhibitor may be administered in either single or multiple doses (e.g., twice or three times a day).

In another embodiment, the PI3K Delta or dual PI3K Delta and Gamma inhibitor and at the PDE4 inhibitor are each administered in an amount ranging from about 0.01 mg to about 1000 mg.

In yet another embodiment, from about 0.05 mg to about 7 g of the PI3K Delta or PI3K Delta and Gamma dual inhibitor and from about 7 to about 7000 mcg (e.g., from about 10 to about 1000 mcg) of the PDE4 inhibitor are administered daily. For example, when the PDE4 inhibitor is roflumilast, from about 100 to about 2000 mcg of roflumilast is administered daily (preferably orally or by inhalation). In another embodiment, about 200, 300, 400, 500, or 600 mcg of roflumilast is administered daily (preferably orally or by inhalation).

The PI3K Delta or PI3K Delta and Gamma dual inhibitor and PDE4 inhibitor may be administered orally or by inhalation. In one embodiment, the PI3K Delta or PI3K Delta and Gamma dual inhibitor is administered by inhalation and the PDE4 inhibitor is administered orally. In another embodiment, the PI3K Delta or PI3K Delta and Gamma dual inhibitor and the PDE4 inhibitor are both administered orally. In yet another embodiment, the PI3K Delta or PI3K Delta and Gamma dual inhibitor is administered orally and the PDE4 inhibitor is administered by inhalation. In another embodiment, the PI3K Delta or PI3K Delta and Gamma dual inhibitor and the PDE4 inhibitor are both administered by inhalation.

In additional embodiments of any of the methods described herein, the PI3K Delta or dual PI3K Delta and Gamma inhibitor and at the PDE4 inhibitor are administered either as oral or by inhalation For example, Both the PI3K Delta or dual PI3K Delta and Gamma inhibitor can and the PDE4 inhibitor is administered orally. Both the PI3K Delta or dual PI3K Delta and Gamma inhibitor can and the PDE4 inhibitor is administered by inhalation, One of the PI3K Delta or dual PI3K Delta and Gamma inhibitor is adminsiated orally and the PDE4 inhibitor is administered by inhalation or One of the PI3K Delta or dual PI3K Delta and Gamma inhibitor is adminsiated by inhalation and the PDE4 inhibitor is administered orally.

In additional embodiments of any of the methods described herein, the PI3K Delta or dual PI3K Delta and Gamma inhibitor and the PDE4 inhibitor are administered at a ratio of about 1:100 to about 100:1 by weight.

In one embodiment, the therapeutically effective amount of PI3K Delta or dual PI3K Delta and Gamma inhibitor is administered twice daily to once every three weeks, and the therapeutically effective amount of the PDE4 inhibitor is administered twice daily to once every three weeks.

Examples of immune disorders which can be treated by the compounds of the present invention include, but are not limited to, psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

A further embodiment of the present invention relates to a method of treating an disease or disorder selected from respiratory diseases and conditions such as diseases of the airways and lungs which are accompanied by increased or altered production of mucus and/or inflammatory and/or obstructive diseases of the airways such as acute bronchitis, chronic bronchitis, chronic obstructive bronchitis (COPD), cough, pulmonary emphysema, allergic or non-allergic rhinitis or sinusitis, chronic sinusitis or rhinitis, nasal polyposis, chronic rhinosinusitis, acute rhinosinusitis, asthma, allergic bronchitis, alveolitis, Farmer's disease, hyperreactive airways, bronchitis or pneumonitis caused by infection, e.g. by bacteria or viruses or helminthes or fungi or protozoons or other pathogens, pediatric asthma, bronchiectasis, pulmonary fibrosis, adult respiratory distress syndrome, bronchial and pulmonary edema, bronchitis or pneumonitis or interstitial pneumonitis caused by different origins, e.g. aspiration, inhalation of toxic gases, vapors, bronchitis or pneumonitis or interstitial pneumonitis caused by heart failure, X-rays, radiation, chemotherapy, bronchitis or pneumonitis or interstitial pneumonitis associated with collagenosis, e.g. lupus erythematodes, systemic scleroderma, lung fibrosis, idiopathic pulmonary lung fibrosis (IPF), interstitial lung diseases or interstitial pneumonitis of different origin, including asbestosis, silicosis, M. Boeck or sarcoidosis, granulomatosis, cystic fibrosis or mucoviscidosis, or a-1-antitrypsin deficiency; or selected from inflammatory diseases and conditions such as inflammatory diseases of the gastrointestinal tract of various origins such as inflammatory pseudopolyps, Crohn's disease, ulcerative colitis, inflammatory diseases of the joints, such as rheumatoid arthritis, or allergic inflammatory diseases of the oro-nasopharynx, skin or the eyes, such as atopic dermatitis, seasonal and perenial, chronic uritcaria, hives of unknown cause and allergic conjunctivitis; and in particular selected from asthma, allergic and non-allergic rhinitis, COPD and atopic dermatitis; comprising administering a therapeutically effective amount of a pharmaceutical composition according to any of the embodiments described herein to a patient in need thereof.

A further embodiment of the present invention relates to the use of a pharmaceutical composition according to any of the embodiments described herein for the manufacture of a medicament for treating respiratory and/or inflammatory diseases and conditions, particularly wherein the respiratory and/or inflammatory diseases or conditions are selected from asthma, allergic and non-allergic rhinitis, COPD and atopic dermatitis.

A further embodiment of the present invention relates to a pharmaceutical composition according to any of the embodiments described herein for use in the treatment of respiratory and inflammatory diseases and conditions, particularly wherein the respiratory and inflammatory diseases or conditions are selected from asthma, allergic and non-allergic rhinitis, COPD and atopic dermatitis.

The present invention is now further illustrated by means of the following non-limiting examples.

EXAMPLES

As described in the following examples, Compound A is roflumilast; Compound B is IC87114; Compound C is Example 74 of International Publication No. WO 11/055215 (PCT/2010/002804) and Compound A1 is Example 7 of International Publication No. WO 2012/151525 (PCT/US2012/036594). The representative examples use roflumilast and aprelimilast as the PDE-4 inhibitor.

Example 1

Combination Studies of a PI3K Delta Inhibitor and a PDE-4 Inhibitor

Compound A was used as the PDE4 inhibitor and compounds B and C were used as the PI3K Delta inhibitor in these studies.

Estimation of TNFα: U937 cells were plated at 100,000 cells per well in a 96 well plate and incubated with the desired concentration of compounds for 30 minutes prior to the addition of 1 µg/ml LPS. Supernatants were collected after 24 hours and estimated for TNFα concentration by ELISA as per the protocol recommended by the kit manufacturer (eBioscience, USA). Briefly, Nunc Maxisorp plates were coated with 100 µl of 1 mg/ml TNFα coating antibody. Supernatant was transferred to plates and incubated at 37° C. for 2 h. Anti-TNFα detection antibody and avidin-HRP were added followed by TMB substrate. Absorbance was measured at 450 nm on Fluostar Omega (BMG Labtech, NC, USA).

Results: The results are shown in FIG. 1. Combining 10 µM of Compound A (roflumilast) with 300 or 30 nM of Compound B (IC87114) effectively reduced TNFα release with an Emax of 75% and 58% respectively. Significant reductions ($p<0.01$) in TNFα secretion were observed with concentrations as low as 300 nM of Compound A combined with 300 nM Compound B indicating that roflumilast in the presence of a PI3Kδ inhibitor controls the regulation of cytokines responsible for exacerbation of COPD.

Quantification of Matrix Metalloproteinase (MMP)-9: Gelatinase activity of MMP-9 was determined by zymography. Proteins in supernatant (after incubation of THP-1 cells with 50 ng PMA for 24 h) were separated on gels containing 0.1% gelatin (Sigma, USA). Gels were re-natured by incubation in 2.5% Triton X-100 for 30 min, incubated overnight in substrate buffer (50 mMTris-HCl, pH 7.5) containing 10 mM $CaCl_2$ and 0.05% $ZnCl_2$ at 37° C. and stained with Coomassie brilliant blue (0.5%). Clear areas in the blue background of the gels demonstrated the presence of gelatinase activity. Molecular weight markers (Fermentas, Lithuania) were run with each gel. Band intensity was calculated using ImageJ 1.42 (NIH, USA).

Figure 2:
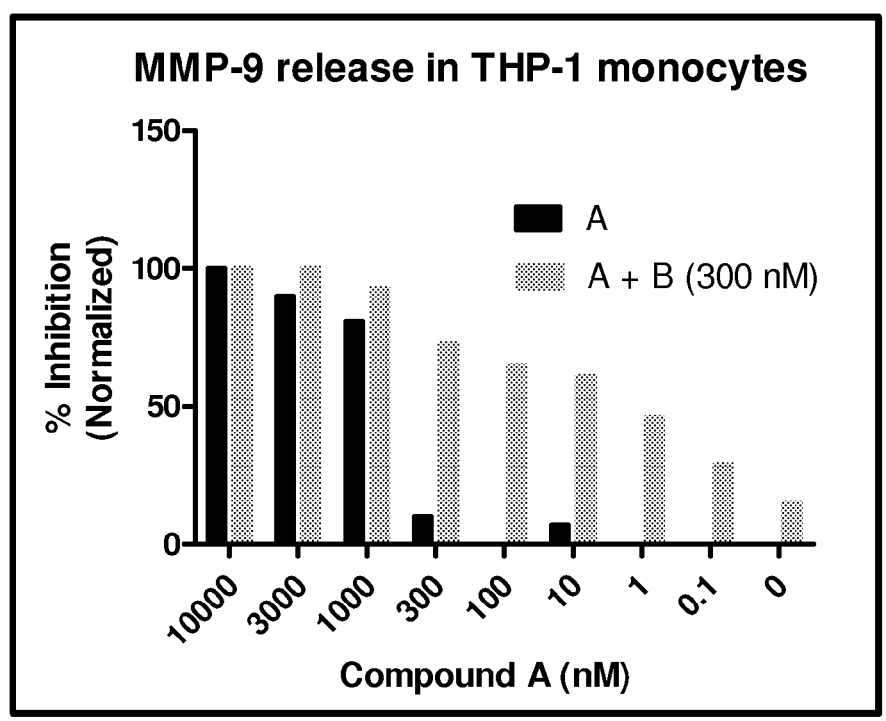
FIG. 2 depicts the effect of Compound A and its combination with Compound B at 300 nM on MMP-9 release from THP-1 cells.

Results: The results are shown in FIG. 2. A two fold increase in MMP-9 release due to induction was observed compared to the blank wells. The $IC_{50}$ of Compound A for the reduction of MMP-9 was 577 nM while Compound B alone had no effect on the MMP-9 release at 300 nM. However, the presence of Compound B (300 nM) with Compound A, effectively potentiated the effect of Compound A even at the lowest concentration tested (0.1 nM).

SDS-PAGE for the Estimation of Phospho-Akt: U-937 monocytes were differentiated into macrophages by incubation with 50 ng/ml PMA for 48 h. Cells were trypsinized and plated at a density of 100,000 per well and stimulated with CSE for 2 h in starvation media. Lysates were made using RIPA buffer and run by SDS-PAGE, transferred to PVDF membrane and probed with phospho-Akt (S473) antibody (Cell signaling, USA) followed by anti-rabbit IgG (Cell signaling, USA). Band intensity was calculated using ImageJ 1.42 (NIH, USA).

Figure 3:
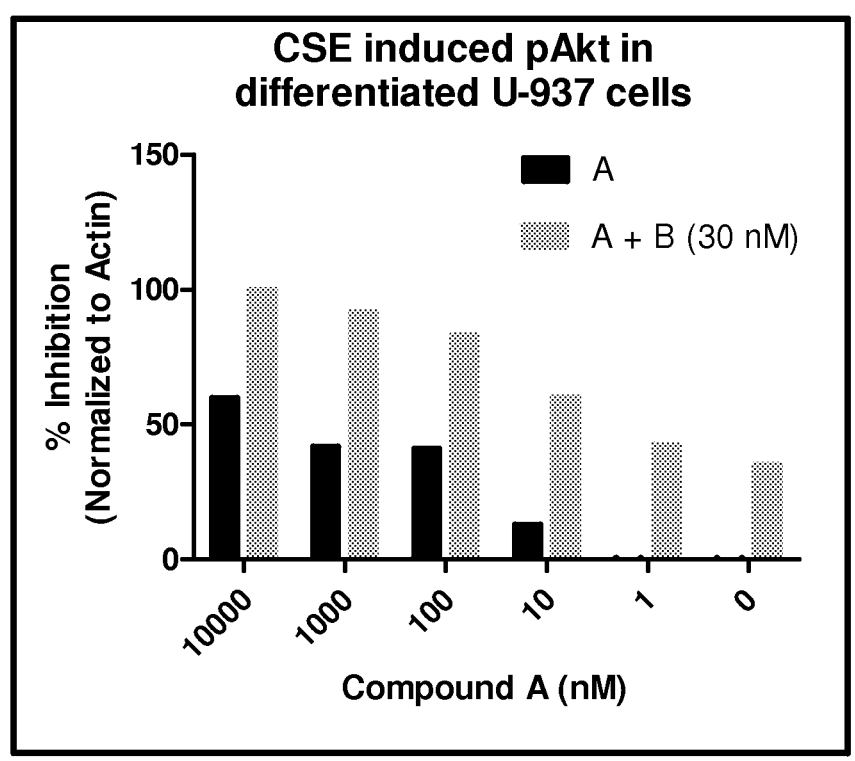
FIG. 3 depicts the effect of Compound A with and without Compound B (30 nM) on pAkt (S473) expression in differentiated U937 cells stimulated with Cigarette Smoke Extract (CSE).

Results: The results are shown in FIG. 3. Individually, Compound A and Compound B dose-dependently inhibited Akt phosphorylation with $IC_{50}$ values of 1934 and 780 nM, respectively. However, in combination with 30 nM of Compound B, a significant reduction (~1290 fold) in the $IC_{50}$ of Compound A (1.5 nM) was observed, indicating accentuation of the response in line with MMP-9 reduction.

Quantification of Neutrophil Elastase: Blood was procured from a local blood bank. Neutrophils were obtained using the dextran sedimentation method. Cells were plated at 100,000 cells per well in a 96-well plate, treated with fMLP (1 µM) and N-Succinyl-Ala-Ala-Ala-p-nitroanalide (1 µM) (Sigma) and incubated for 2 h. Intensity of digested substrate after incubation was determined by measuring the absorbance at 405 nm on a Fluostar Omega (BMG Labtech, NC, USA).

Figure 4:
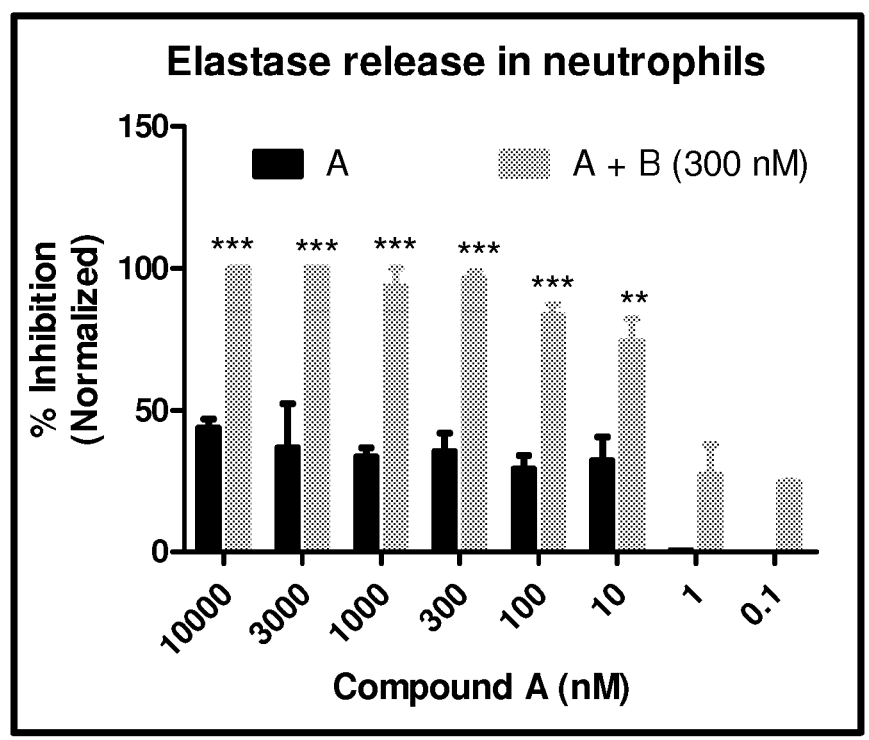
FIG. 4 depicts the effect of Compound A and its combination with Compound B (300 nM) on the inhibition of release of elastase from human neutrophils. $p<0.01$ and *$p<0.001$ (versus Compound A).

Results: The results are shown in FIG. 4. Compound A inhibited fMLP induced elastase release with an $IC_{50}$ of 10.2 nM (Emax=43%) while the reduction with Compound B alone was negligible (10% at 300 nM). Combining Compound A with 300 nM of Compound B resulted in an increase in Emax (65%) along with a corresponding reduction in $IC_{50}$ of Compound A to 4.8 nM.

Cell Proliferation Assay: A549 cells were plated at 10,000 cells per well in a 96-well plate and incubated with CSE for 72 h. Viability of cells was determined by estimating the amount of soluble formazan (in DMSO) formed after addition of 100 µg MTT and a 4 h incubation at 37° C. Media was removed and the crystals were dissolved in 100 µl DMSO. Absorbance was measured at 450 nm on a Fluostar Omega (BMG Labtech, NC, USA).

Figure 5:
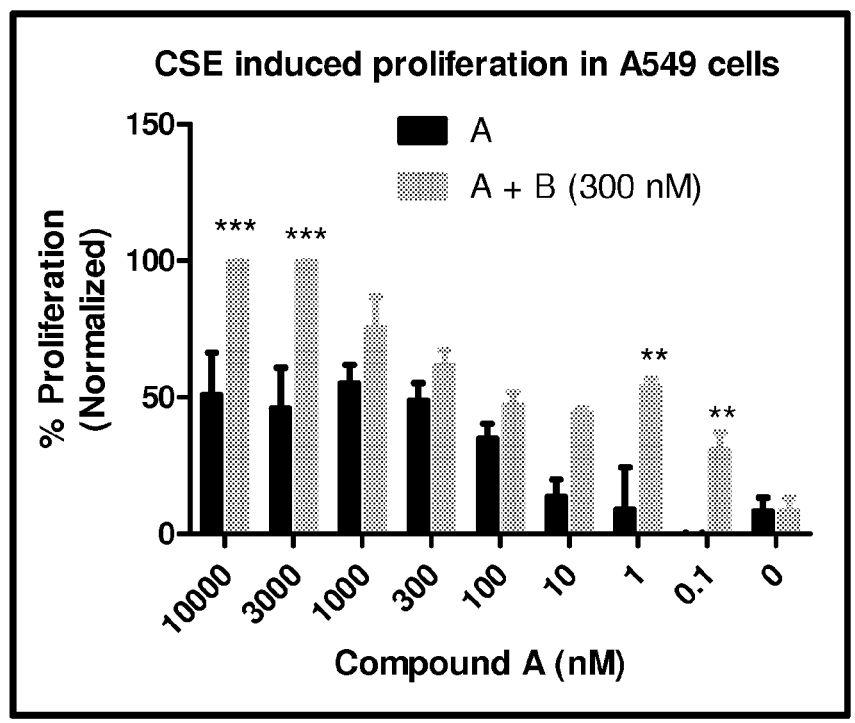
FIG. 5 depicts the effect of Compound A and its combination with Compound B (300 nM) on the proliferation of A549 cells after CSE induction. * represents $p<0.05$,  represents $p<0.01$ and * represents $p<0.001$ when compared to administration of Compound A alone.

Results: The results are shown in FIG. 5. The combination of Compound A and 300 nM of Compound B caused a marked reversal of the anti-proliferative effect of CSE with an $IC_{50}$ of 8.7 nM. Without wishing to be bound by any particular theory, the inventors theorize that the combination of a PDE4 inhibitor and a PI3Kδ inhibitor serves to protect the lung alveolar epithelium, thereby minimizing the progression of COPD.

Cell Cycle Analysis: A549 cells were plated in 6-well plates at a density of 100,000 cells per well and stimulated with CSE for 72 h. After incubation, cells were fixed in 70% ethanol and stored at 4° C. till analysis. Cells were stained with Guava Cell Cycle reagent according to the manufacturer's instructions. Cell cycle data were obtained using the Guava Personal Cell Analysis System (Millipore, USA).

Figure 6:
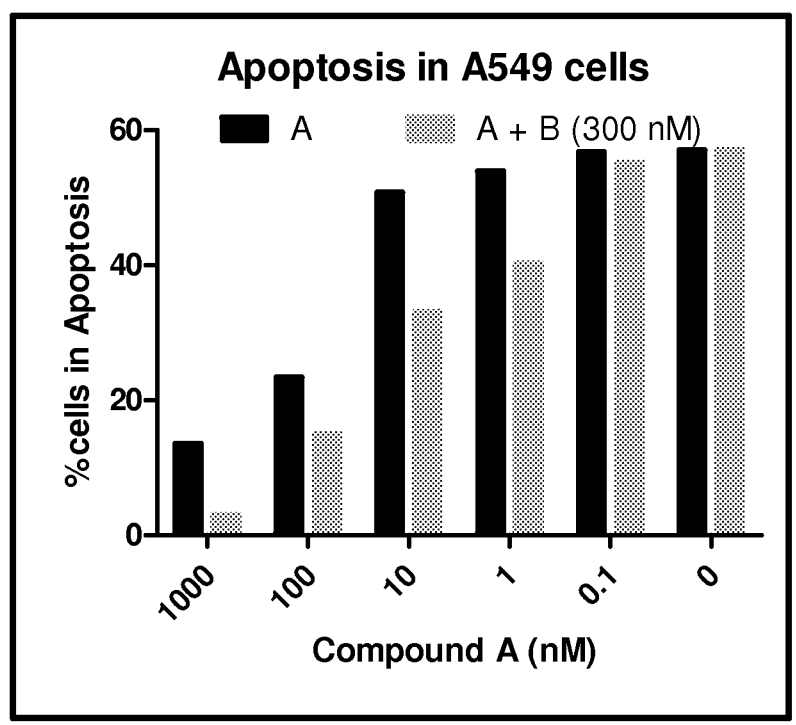
FIG. 6 depicts the inhibition of apoptosis in A549 cells by Compound A and its combination with Compound B (300 nM).

Results: The results are shown in FIG. 6. Treatment with Compound A resulted in a dose-dependent inhibition of apoptosis. This decrease was significantly further potentiated using a combination of Compound A with 300 nM of Compound B, indicating the potential utility of this combination in preventing lung damage.

In summary, the inhibition of TNFα, pAkt, and MMP-9 in differentiated U937 macrophages upon stimulation with LPS/CSE was determined. Neutrophil functionality manifested by a modulation of elastase activity was estimated. The protective effect of the combination (Compounds A and B) on CSE induced apoptosis of lung epithelial cells was also determined. The data demonstrates that the combination of Compound A (PDE4 inhibitor) and Compound B (PI3K delta inhibitor) reduces TNFα, pAkt and MMP-9 at nanomolar concentrations and is several fold more potent than either of the compounds alone. Inhibition of neutrophil elastase was also increased significantly with the combination, thereby providing evidence for the therapeutic benefits of the combination of a PI3K delta inhibitor and a PDE4 inhibitor in the treatment of COPD.

LPS Induced TNFα in Human Whole Blood (HWB): Freshly collected HWB was diluted with media and incubated with the desired concentration of inhibitor for 15 min. LPS (1 μg/ml) was added and then incubated for 24 hours. The supernatant was collected and TNFα estimated using an eBioscience TNFα ELISA kit. While administration of 1000 nM of Compound C or 2.5 nM of roflumilast alone, did not cause an appreciable response (<10% decrease of TNFα secretion), the combination of the two compounds, when administered at the same concentration, resulted in a >30% decrease of TNFα secretion, i.e., greater than a 3-fold increase in potency for the combination when compared with the potency of Compound C or roflumilast when administered alone, thereby indicating a synergistic effect and therapeutic relevance of this combination in the treatment of inflammatory disorders, in particular airway disorders, psoriasis and RA.

LPS Induced TNFα in PBMC: PBMC (peripheral blood mononuclear cells) from whole blood were isolated by density gradient using Histopaque and incubated with the desired concentration of inhibitor for 15 minutes. LPS (1 μg/ml) was added and then incubated for 24 hours. The supernatant was collected and TNFα estimated using an eBioscience TNFα ELISA kit. While administration of 1000 nM of Compound C alone caused a 20% decrease of TNFα secretion, addition of 1.25 nM roflumilast to 1000 nM of Compound C resulted in a 80% decrease of TNFα secretion, i.e., a 4-fold increase in potency compared to the potency of Compound C alone, thereby indicating the synergistic effect and therapeutic relevance of this combination in the treatment of inflammatory disorders, in particular airway disorders, psoriasis and RA.

Lipopolysaccharide Induced Pulmonary Neutrophilia in Female Wistar Rats: An exaggerated recruitment and subsequent activation of neutrophil is likely to be important for the development and course of several inflammatory diseases in the airways and lungs, such as severe asthma, COPD, cystic fibrosis, and acute respiratory distress syndrome. The mechanisms by which neutrophils contribute to these diseases may involve the release of proteolytic enzymes, such as neutrophil elastase, and free oxygen radicals. When released, these agents can cause bronchoconstriction, bronchial hyperreactivity, hyper-secretion, epithelial damage, and tissue remodelling in the airways.

After the quarantine period, fasted animals were randomized and divided into groups depending on their body weights. Test compound was prepared as a suspension in a vehicle consisting of 0.5% methylcellulose in which Tween 80 was used as a suspending agent. Compounds or vehicle were administered by oral gavage in a volume of 10 mL/kg. Animals were anaesthetized with ketamine and LPS solution was administered intratracheally 30 minutes after compound administration at a dose of 1 mg/kg. Six hours after LPS instillation, animals were exsanguinated under anaesthesia, and the trachea was cannulated, and lungs were lavaged with 5-ml aliquots of heparinised PBS (1 unit/ml) four times through the tracheal cannula (total volume 20 ml). Bronchioalveolar (BAL) fluid was stored at 2-8° C. until assayed for total cell and differential leukocyte count. BAL fluid was centrifuged (500×g for 10 min) and the resulting cell pellet was resuspended in 0.5 ml of heparinised saline. The total numbers of white blood cells were determined in BAL fluid or blood using a cell counter and were adjusted to $1 \times 10^6$ cell/ml. Differential cell count was calculated manually. One hundred microliters of the cell suspension was centrifuged using cytospin 3 to prepare a cell smear. The cell smear was stained with a blood staining solution for differentiation and slides were microscopically observed to identify eosinophils according to their morphological characteristics. The number of each cell type among 300 white blood cells in the cell smear was determined and expressed as a percentage of total cells. The number of eosinophil in BALF was calculated.

Figure 7A:
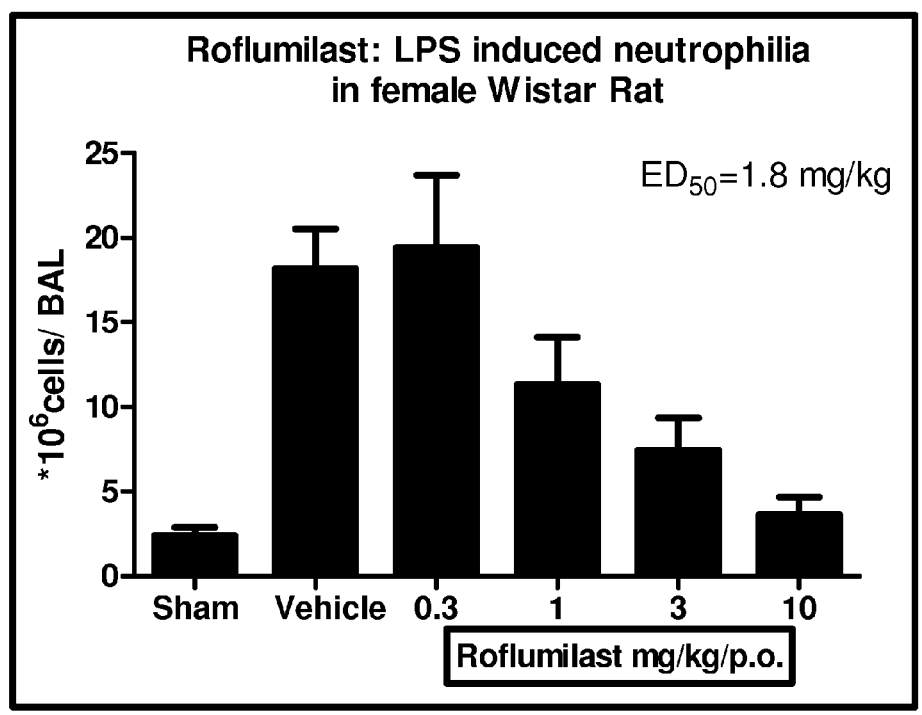
FIGS. 7A, 7B, and 7C depict the inhibition in neutrophil infiltration by Compound A, Compound C and their combination, respectively.
Figure 7B:
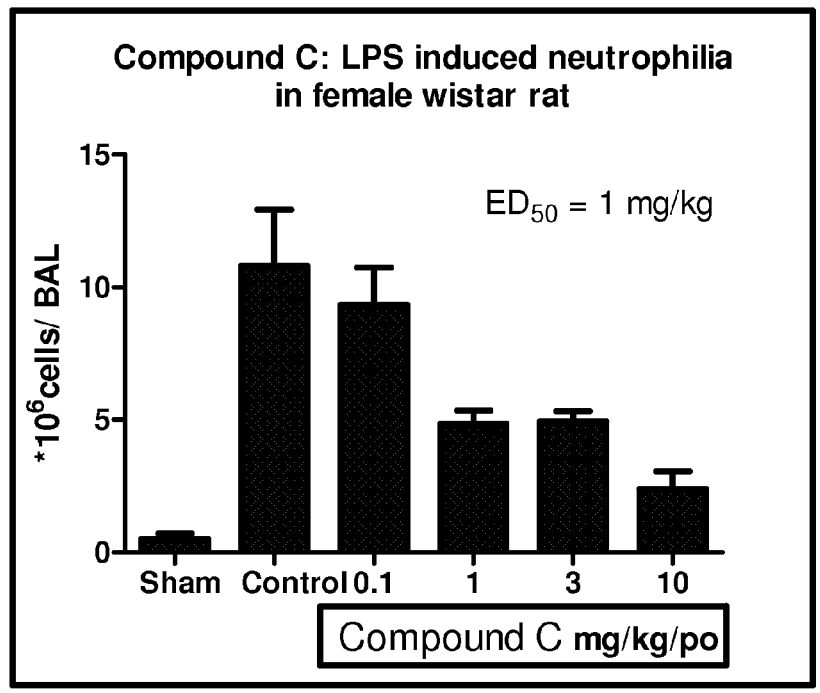
Figure 7C:
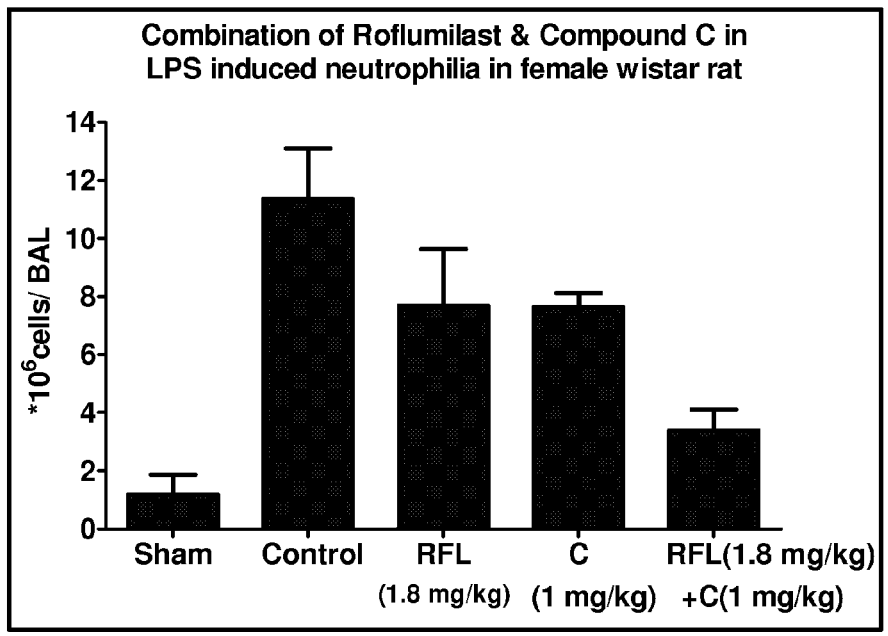

Results: The results are shown in FIGS. 7A, 7B, and 7C.

Effective Dose of Roflumilast: Roflumilast demonstrated a dose dependent inhibition in neutrophil infiltration compared to the control group at 0.3, 1, 3 and 10 mg/kg. Percent inhibitions were −7.89%, 43.46%, 68.02%, and 92.21% respectively and the 50% inhibition ($ED_{50}$) dose was 1.8 mg/kg.

Effective Dose of Compound C: A dose dependent inhibition in neutrophil infiltration compared to control group was observed at 0.1, 1, 3 and 10 mg/kg upon oral administration of Compound C. Percent inhibitions were 14.15%, 57.76%, 56.93%, and 81.55% respectively and the 50% inhibition ($ED_{50}$) dose was 1 mg/kg.

Combination of Each ED50 Dose of Roflumilast and Compound C: Roflumilast or Compound C alone showed 36.18% and 36.56% inhibition of neutrophil infiltration at doses of 1.8 and 1 mg/kg respectively compared to the control group. When roflumilast (1.8 mg/kg) was combined with Compound C (at a dose of 1 mg/kg), inhibition of neutrophil infiltration increased to 78.20% compared to the control group animals.

Acute Cigarette Smoke Induced Cell Infiltration in Male Balb/c Mice: Animals were acclimatized for seven days prior to the start of the experiment. Animals were randomly distributed to various groups based on their body weights. On day 1, mice were administered by test compound or vehicle by the oral route and after 30 mins test compound administration animals were placed in a whole body exposure box. The mice were exposed to the mainstream smoke of 6 cigarettes from day 1 to day 4. Exposure to the smoke of each cigarette lasted for 10 min (cigarettes were completely burned in the first two minutes and followed by an air flow with animal ventilator) followed by exposure for the next 20 min with fresh room air. After every second cigarette an additional break of 20 min with exposure to fresh room air was conducted. Control animals were exposed to the room air chamber. From day 1 to day 4 animals were administered test compound by the oral route. On day 5, 24 hours after the last cigarette smoke (CS) exposure animals were exsanguinated under anaesthesia, and the trachea was cannulated and the lungs were lavaged with 0.5 ml aliquots of heparinised PBS (1 unit/ml) four times through a tracheal cannula (total volume 2 ml). Bronchioalveolar (BAL) collected was stored at 2-8 OC until assayed for total cell and differential leukocyte count. BAL fluid was centrifuged (500×g for 10 min) and the resulting cell pellet was resuspended in 0.5 ml of heparinised saline. The total number of white blood cells was determined in BAL fluid and blood using a blood cell counter and adjusted to $1 \times 10^6$ cell/ml. Differential cell count was calculated manually. Forty microliters of the cell suspension was centrifuged using cytospin 3 to prepare a cell smear. The cell smear was stained with a blood staining solution for differentiation and microscopically observed by identifying each cell according to its morphological characteristics. The number of each cell type among 300 white blood cells in the cell smear were determined and expressed as a percentage, and the number of neutrophils and macrophages in each BAL fluid were calculated.

Figure 9:
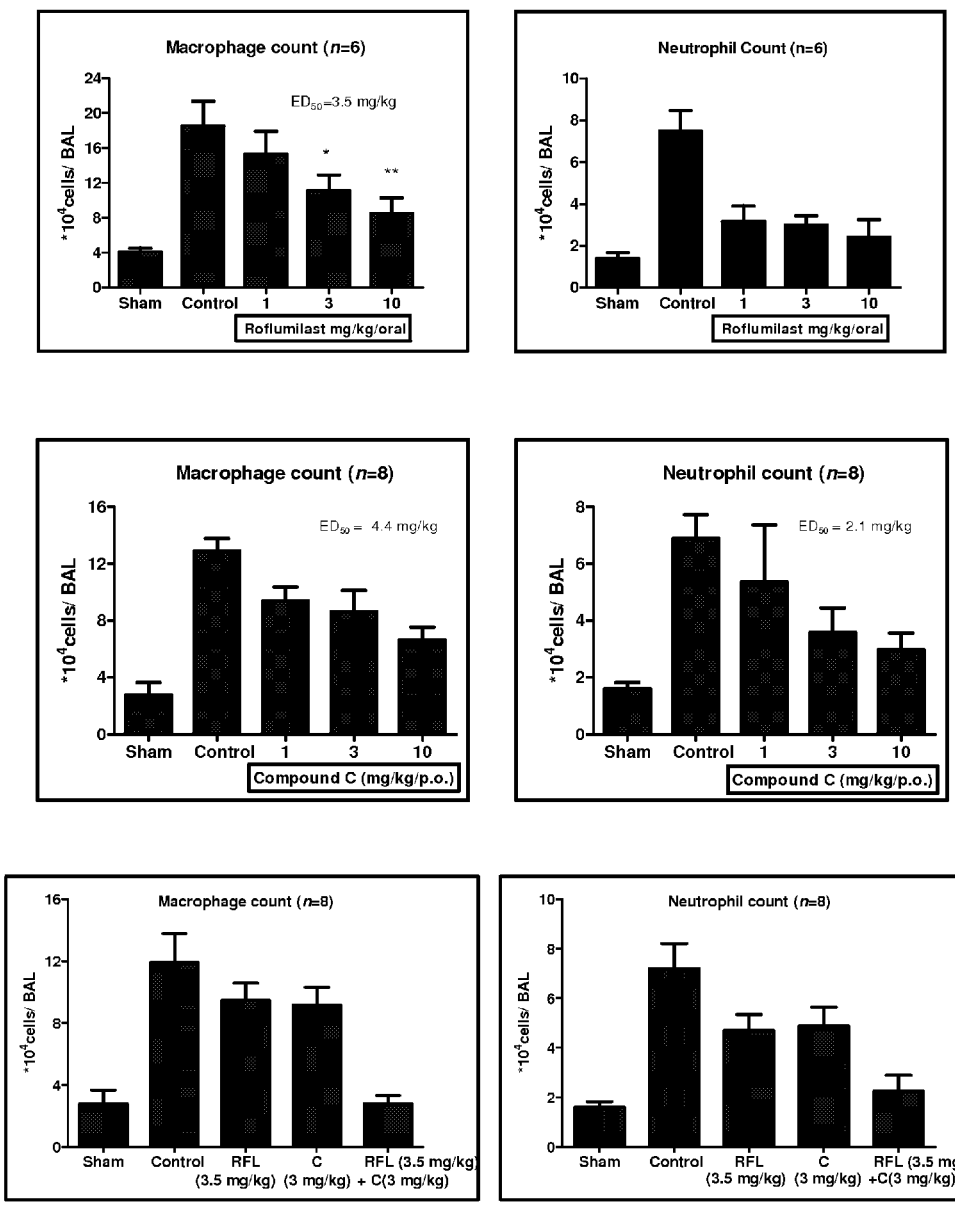
FIG. 9 depicts the inhibition in macrophage infiltration for Compound A, Compound C and their combination in acute cigarette smoke induced cell infiltration in Male Balb/c mice.

Results: The results are shown in FIG. 9.

Effective Dose of Roflumilast: Roflumilast demonstrated a dose dependent inhibition in macrophage infiltration compared to the control group at 1, 3 and 10 mg/kg. Percent inhibitions were 22.2%, 51.00%, and 69.11% respectively and the 50% inhibition ($ED_{50}$) dose was 3.5 mg/kg. Roflumilast demonstrated inhibition in neutrophil infiltration compared to the control group at 1, 3 and 10 mg/kg. Percent inhibitions were 70.85%, 73.69%, and 83.01% respectively and the dose of 50% inhibition (ED50) of neutrophil infiltration was considered for combination study.

Effective Dose of Compound C: A dose dependent inhibition in macrophage and neutrophil infiltration compared to the control group was observed at 1, 3 and 10 mg/kg upon oral administration of Compound C. Percent inhibitions of macrophage infiltrations were 34.84%, 42.09%, and 61.77% respectively and the 50% inhibition (ED50) dose was 4.4 mg/kg. Compound C demonstrated inhibition in neutrophil infiltration compared to the control group at 1, 3 and 10 mg/kg. Percent inhibitions were 29.06%, 62.38%, and 74.25% respectively and the dose of 50% inhibition (ED50) of neutrophil infiltration was 2.1 mg/kg.

Combination of Each ED50 Dose of Roflumilast & Compound C:

Roflumilast or Compound C alone showed 26.55% and 30.01% inhibition of macrophage infiltration at doses of 3.5 and 3 mg/kg respectively compared to the control group. When roflumilast (3.5 mg/kg) was combined with Compound C (at a dose of 3 mg/kg), inhibition of macrophage infiltration increased to 99.89% compared to the control group animals. Roflumilast or Compound C alone showed 44.42% and 41.47% inhibition of neutrophil infiltration at doses of 3.5 and 3 mg/kg respectively compared to the control group. Similarly, the combination of roflumilast (3.5 mg/kg) and Compound C (at a dose of 3 mg/kg) showed 88.34% inhibition of neutrophil infiltration compared to the control group.

Chronic Cigarette Smoke Induced Cell Infiltration in Male Balb/c Mice: Animals were acclimatized for seven days prior to the start of the experiment. Animals were randomly distributed to various groups based on their body weights. Mice were exposed to the mainstream smoke of 4 cigarettes from day 1 to day 11. Exposure to the smoke of each cigarette lasted for 10 min (each cigarette was completely burned in the first two minutes, followed by an air flow with animal ventilator) and were exposed for the next 20 min with fresh room air. After every second cigarette an additional break of 20 min with exposure to fresh room air was conducted. Control animals were exposed to the room air chamber. Test compound was administered by the oral route from day 6 to day 11 before 30 mins whole body smoke exposure. On day 12, 24 hours after the last cigarette smoke (CS) exposure animals were exsanguinated under anaesthesia, and the trachea was cannulated and the lungs were lavaged with 0.5 ml aliquots of heparinised PBS (1 unit/ml) four times through tracheal cannula (total volume 2 ml). Bronchioalveolar (BAL) collected was stored at 2-8 OC until assayed for total cell and differential leukocyte count. BAL fluid was centrifuged (500×g for 10 min) and the resulting cell pellet was resuspended in 0.5 ml of heparinised saline. The total number of white blood cells was determined in BAL fluid and blood using a blood cell counter and adjusted to $1 \times 10^6$ cell/ml. Differential cell count was calculated manually. Forty microliters of the cell suspension was centrifuged using cytospin 3 to prepare a cell smear. The cell smear was stained with a blood staining solution for differentiation and microscopically observed by identifying each cell according to its morphological characteristics. The number of each cell type among 300 white blood cells in the cell smear was determined and expressed as a percentage, and the number of neutrophils and macrophages in each BAL fluid were calculated.

Figure 11:
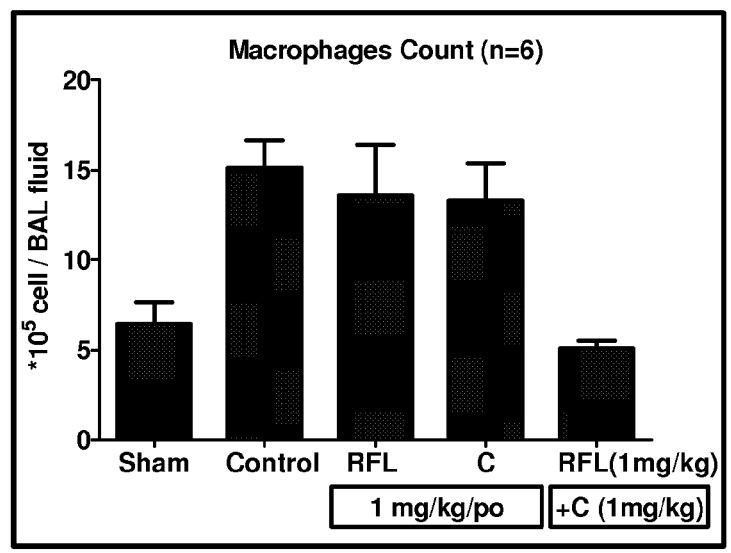
FIG. 11 depicts the inhibition in macrophage infiltration for Compound A, Compound C and their combination in chronic cigarette smoke induced cell infiltration in Male Balb/c mice.
Figure 11:
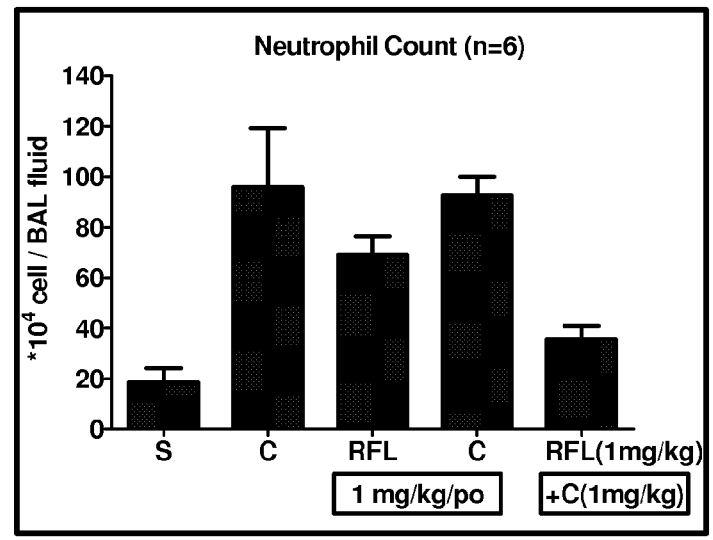

Results: The results are shown in FIG. 11.

Combination of Each $ED_{50}$ Dose of Roflumilast & Compound C: Roflumilast or Compound C alone showed 6.30% and −13.30% inhibition of macrophage infiltration at dose of 1 and 1 mg/kg respectively compared to the control group. When roflumilast (1 mg/kg) was combined with Compound C (at a dose of 1 mg/kg), inhibition of macrophage infiltration increased to 122.24% compared to the control group animals. Roflumilast or Compound C alone showed 34.60% and 4.08% inhibition of neutrophil infiltration at dose of 1 mg/kg and 1 mg/kg respectively compared to the control group. Similarly, the combination of roflumilast (1 mg/kg) and Compound C (at a dose of 1 mg/kg) showed 77.78% inhibition of neutrophil infiltration compared to the control group.

Example 2

Combination Studies of a Dual PI3K Delta and Gamma Inhibitor and PDE-4 Inhibitor This study was conducted using Compound A1 as the dual PI3K Delta and Gamma inhibitor. Compound A1 exhibits an $IC_{50}$ value of ≤40 nM for both the PI3K Delta and PI3K Gamma enzymes.

LPS Induced TNFα in MH-S (Mouse Alveolar Macrophage) Cells: MH-S represents a mouse alveolar macrophage cell line that secretes copious amounts of TNFα upon induction by LPS. Cells were plated at 150,000 cells per well. 10 nM of Compound A1 (final concentration) was added 15 minutes prior to the addition of roflumilast. LPS (1 μg/ml) was added and then incubated for 4 hours. The supernatant was collected after 20 hours and TNFα was estimated using an ELISA kit. Compound A1 dose-dependently inhibited TNFα, a prominent cytokine involved in the progression of COPD. Addition of 30 nM of Compound A1 to the PDE4 inhibitor roflumilast resulted in a several-hundred fold reduction in $IC_{50}$ compared to the $IC_{50}$ of roflumilast alone, thereby indicating the synergy and therapeutic relevance of this combination in airway disorders. Similarly, while administration of 15 nM of Compound A1 or 130 nM of aprelimilast alone did not caused an appreciable decrease in TNFα (~10%) secretion, the combination of the two compounds at the same concentrations resulted in a greater than 35% reduction, thus providing the synergistic and therapeutic relevance of this combination in the treatment of inflammatory disorders, in particular airway disorders, psoriasis and RA.

LPS Induced TNFα in THP-1 (Human Monocyte) Cells: THP-1 represents a monocytic cell line that has elevated endogenous pAKT levels and secretes copious amounts of TNFα upon induction by LPS. Cells were plated at 150,000 cells per well. 10 nM of Compound A1 (final concentration) was added 15 minutes prior to the addition of roflumilast. LPS (1 μg/ml) was added and then incubated for 4 hours.

The supernatant was collected after 20 hours and TNFα was estimated using an ELISA kit. Compound A1 dose-dependently inhibited TNFα, a prominent cytokine involved in the progression of COPD. Addition of 100 nM Compound A1 to the PDE4 inhibitor roflumilast resulted in a several-hundred fold reduction in $IC_{50}$ compared to the $IC_{50}$ of roflumilast alone, thereby indicating the synergy and hence the therapeutic relevance of this combination in the treatment of airway disorders.

Con A+PMA Induced IFNγ in Human Whole Blood (HWB): Freshly collected HWB was diluted with media and incubated with the desired concentration of inhibitor for 15 minutes. Cytokine release was induced with the addition of Concanavalin A (25 µg/ml)+Phorbol Myristate Acetate (50 ng/ml). The supernatant was collected after 20 hours and IFNγ was estimated using an ELISA kit. While administration of 10 nM Compound A1 alone did not affect IFNγ secretion, administration of the combination of 10 nM Compound A1 and roflumilast resulted in a 3-fold reduction in $IC_{50}$ compared to the $IC_{50}$ of roflumilast alone, thereby indicating the therapeutic relevance of this combination in the treatment of airway disorders, psoriasis and RA.

LPS Induced TNFα in Human Whole Blood (HWB): Freshly collected HWB was diluted with media and incubated with the desired concentration of inhibitor for 15 minutes. LPS (1 µg/ml) was added and then incubated for 24 hours. The supernatant was collected and TNFα estimated using an eBioscience TNFα ELISA kit. While administration of 100 nM of Compound A1 alone did not affect TNFα secretion, administration of the combination of 100 nM Compound A1 and roflumilast resulted in a more that 10-fold reduction in $IC_{50}$ compared to the $IC_{50}$ of roflumilast alone, thereby indicating the synergy as well the therapeutic relevance of this combination in the treatment of inflammatory disorders, in particular airway disorders, psoriasis and RA.

Con A+PMA Induced IFNγ in PBMC: PBMC from whole blood were isolated by density gradient using Histopaque and incubated with the desired concentration of inhibitor for 15 minutes. Cytokine release was induced with the addition of Concanavalin A (25 µg/ml)+Phorbol Myristate Acetate (50 ng/ml). Supernatant was collected after 20 hours and IFNγ was estimated using an ELISA kit. While administration of 10 nM Compound A1 alone did not affect IFNγ secretion, addition of the combination of 10 nM Compound A1 and roflumilast resulted in a 1.5-fold reduction in $IC_{50}$ compared to the $IC_{50}$ of roflumilast alone, thereby indicating the synergistic effect and the therapeutic relevance of this combination in the treatment of inflammatory disorders, in particular airway disorders, psoriasis and RA.

LPS Induced TNFα in PBMC: PBMC from whole blood were isolated by density gradient using Histopaque and incubated with the desired concentration of inhibitor for 15 minutes. LPS (1 µg/ml) was added and then incubated for 24 hours. The supernatant was collected and TNFα estimated using an eBioscience TNFα ELISA kit. While administration of 10 nM Compound A alone caused a 25% decrease of TNFα secretion, addition of the combination of 10 nM Compound A1 and roflumilast resulted in a 3-fold reduction in $IC_{50}$ compared to the $IC_{50}$ of roflumilast alone, thereby indicating the therapeutic relevance of this combination in the treatment of inflammatory disorders, in particular airway disorders, psoriasis and RA.

Lipopolysaccharide Induced Pulmonary Neutrophilia in Female Wistar Rats: The procedure for LPS induced pulmonary neutrophilia in female Wistar rats as described in Example 1 was performed with compound A1 and roflumilast.

Figure 8A:
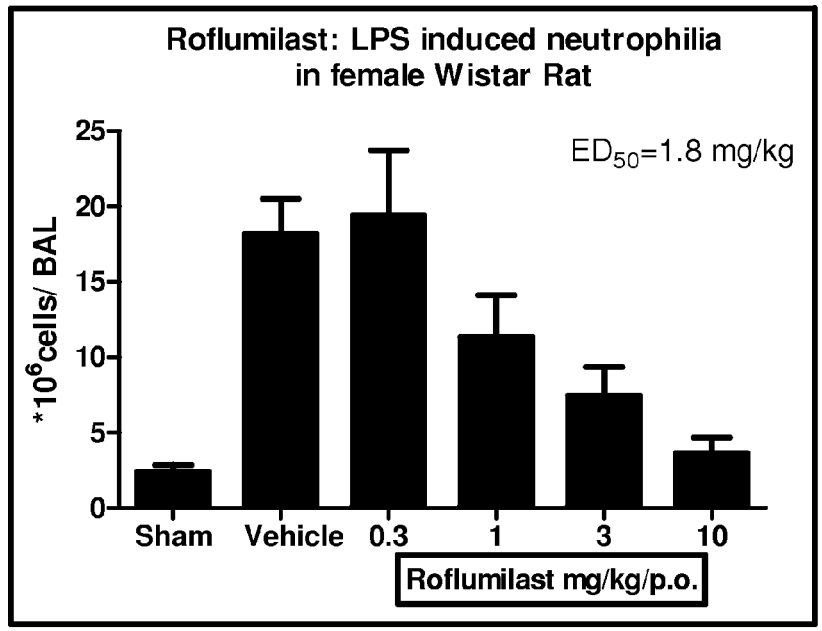
FIGS. 8A, 8B, and 8C depict the inhibition in neutrophil infiltration by Compound A, Compound A1 and their combination.
Figure 8B:
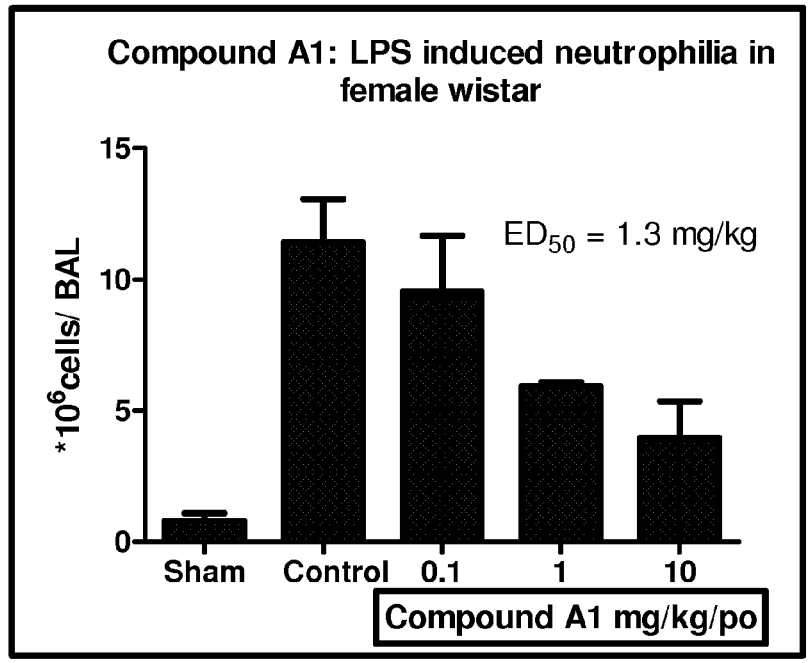
Figure 8C:
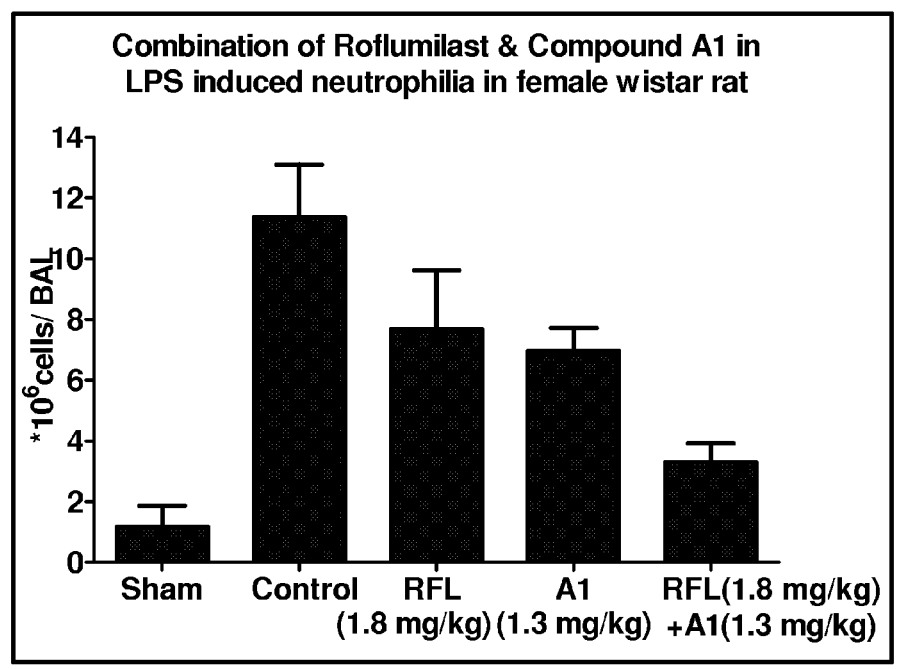

Results: The results are shown in FIGS. 8A, 8B, and 8C.

Effective Dose of Roflumilast: Roflumilast demonstrated a dose dependent inhibition in neutrophil infiltration compared to the control group at 0.3, 1, 3 and 10 mg/kg. Percent inhibitions were −7.89%, 43.46%, 68.02%, and 92.21% respectively and the 50% inhibition ($ED_{50}$) dose was 1.8 mg/kg.

Effective Dose of Compound A1: A dose dependent inhibition in neutrophil infiltration compared to the control group was observed at 0.1, 1, and 10 mg/kg upon oral administration of Compound A1. Percent inhibitions were 17.83%, 51.76%, and 70.21% respectively and the 50% inhibition (ED50) dose was 1.3 mg/kg.

Combination of Each $ED_{50}$ Dose of Roflumilast and Compound A1: Roflumilast or Compound A1 alone showed 36.18% and 43.02% inhibition of neutrophil infiltration at dose of 1.8 and 1.3 mg/kg respectively compared to the control group. When roflumilast (1.8 mg/kg) was combined with Compound A1 (at a dose of 1.3 mg/kg), inhibition of neutrophil infiltration increased to 79.20% compared to the control group animals.

Acute Cigarette Smoke Induced Cell Infiltration in Male Balb/c Mice: The procedure for acute cigarette smoke induced cell infiltration in male Balb/c mice described in Example 1 was performed with Compound A1 and roflumilast.

Figure 10:
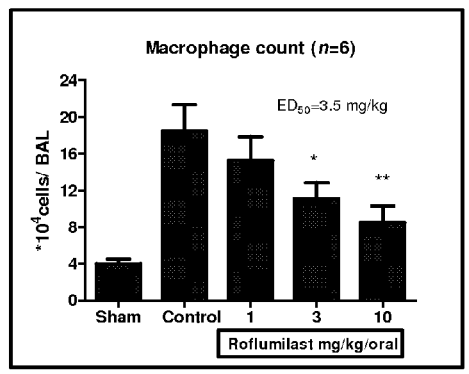
FIG. 10 depicts the inhibition in macrophage infiltration for Compound A, Compound A1 and their combination in acute cigarette smoke induced cell infiltration in Male Balb/c mice.
Figure 10:
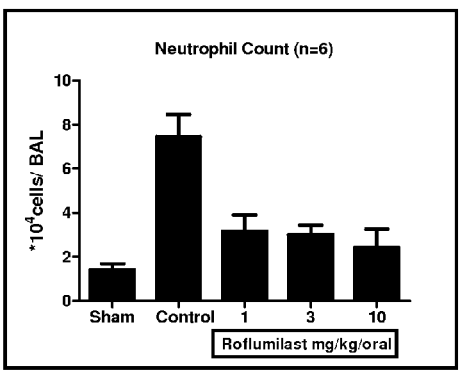
Figure 10:
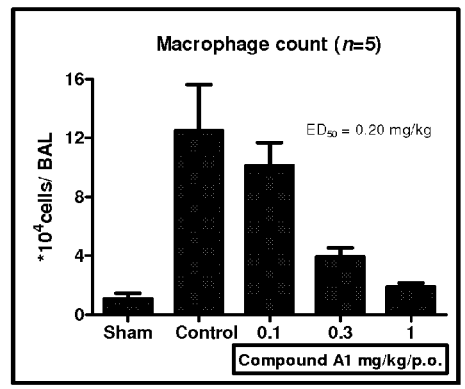
Figure 10:
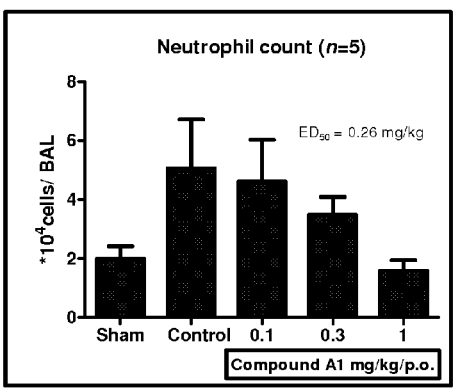
Figure 10:
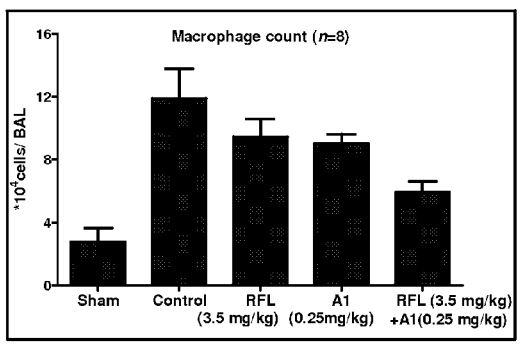
Figure 10:
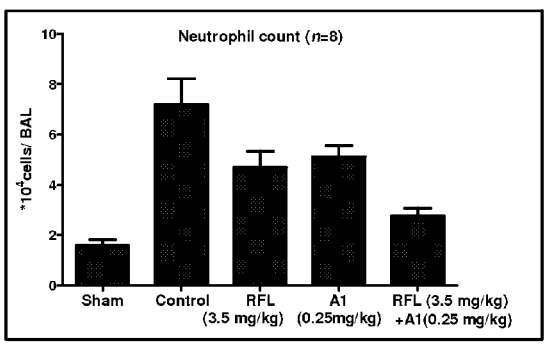

Results: The results are shown in FIG. 10.

Effective Dose of Roflumilast: Roflumilast demonstrated a dose dependent inhibition in macrophage infiltration compared to the control group at 1, 3 and 10 mg/kg. Percent inhibitions were 22.2%, 51.00%, and 69.11% respectively and the 50% inhibition ($ED_{50}$) dose was 3.5 mg/kg. Roflumilast demonstrated inhibition in neutrophil infiltration compared to the control group at 1, 3 and 10 mg/kg. Percent inhibitions were 70.85%, 73.69%, and 83.01% respectively and the dose of 50% inhibition (ED50) of macrophage infiltration was considered for combination study.

Effective Dose of Compound A1: A dose dependent inhibition in macrophage and neutrophil infiltration compared to the control group was observed at 0.1, 0.3 and 1 mg/kg upon oral administration of Compound A1. Percent inhibitions of macrophage infiltrations were 20.60%, 75.19%, and 93.11% respectively and the 50% inhibition (ED50) dose was 0.20 mg/kg. Compound A1 demonstrated inhibition in neutrophil infiltration compared to the control group at 0.1, 0.3 and 1 mg/kg. Percent inhibitions were 14.76%, 51.31%, and 112.83% respectively and the dose of 50% inhibition ($ED_{50}$) of neutrophil infiltration was 0.26 mg/kg.

Combination of Each $ED_{50}$ Dose of Roflumilast & Compound A1: Roflumilast or Compound A1 alone showed 26.55% and 31.33% inhibition of macrophage infiltration at doses of 3.5 and 0.3 mg/kg respectively compared to the control group. When roflumilast (3.5 mg/kg) was combined with Compound A1 (at a dose of 0.25 mg/kg), inhibition of macrophage infiltration increased to 65.52% compared to the control group animals. Roflumilast or Compound A1 alone showed 44.42% and 36.69% inhibition of neutrophil infiltration at doses of 3.5 and 0.25 mg/kg respectively compared to the control group. Similarly, the combination of roflumilast (3.5 mg/kg) and Compound A1 (at a dose of 0.25 mg/kg) showed 79.14% inhibition of neutrophil infiltration compared to the control group.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications, patents and patent applications cited in this application are herein incorporated by reference to the same extent as if each individual publication, patent or patent application was specifically and individually indicated to be incorporated herein by reference.

What is claimed is:

1. A method of treating an autoimmune, respiratory and/or inflammatory disease or condition selected from asthma, chronic obstructive pulmonary disease, rheumatoid arthritis, inflammatory bowel disease, glomerulonephritis, neuroinflammatory diseases, multiple sclerosis, uveitis, psoriasis, arthritis, vasculitis, dermatitis, osteoarthritis, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis, myasthenia gravis, autoimmune hemolytic anemia, cystic fibrosis, chronic relapsing hepatitis, primary biliary cirrhosis, allergic conjunctivitis, atopic dermatitis, and combinations thereof, the method comprising administering to a subject in need thereof a therapeutically effective amount of (i) a PI3K Delta inhibitor or a dual PI3K Delta and Gamma inhibitor, and (ii) a PDE4 inhibitor, wherein the PI3K Delta inhibitor is selected from 2-((6-amino-9H-purin-9-yl)methyl)-5-methyl-3-o-tolylquinazolin-4(3H)-one (IC87114), (S)-2-(1-(9H-purin-6-ylamino)ethyl)-6-fluoro-3-(3-fluorophenyl)-4H-chromen-4-one, and pharmaceutically acceptable salts thereof;

the dual PI3K Delta and Gamma inhibitor is selected from (+)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one and pharmaceutically acceptable salts thereof; and the PDE4 inhibitor is selected from roflumilast, apremilast, N-(3,5-dichloro-1-oxo-pyridin-4-yl)-4-difluoromethoxy-3-cyclopropylmethoxybenzamide, oglemilastum, D-4418, D-4396(Sch-351591), AWD-12-281 (GW-842470), CDP-840, 2-carbomethoxy-4-cyano-4-(3-cyclopropylmethoxy-4-difluoromethoxy phenyl)cyclohexan-1-one, cis [4-cyano-4-(3-cyclopropylmethoxy-4-difluoromethoxy phenyl) cyclohexan-1-ol], cilomilast, cis [4-cyano-4-(3-cyclopentyloxy-4-methoxy phenyl) cyclohexan-1-carboxylic acid], (R)-(+)-ethyl[4-(3-cyclopentyloxy-4-methoxyphenyl) pyrrolidin-2-yliden] acetate, (S)-(−)-ethyl[4-(3-cyclopentyloxy-4-methoxyphenyl)pyrrolidin-2-ylidenl acetate, CDC-801, CDC-3052, lirimilast (Bay-198004), and pharmaceutically acceptable salts thereof.

2. The method according to claim 1, wherein the PDE-4inhibitor is selected from the group consisting of roflumilast, apremilast, and pharmaceutically acceptable salts thereof.

3. The method according to claim 1, wherein the therapeutically effective amount of the PI3K Delta or dual PI3K Delta and Gamma inhibitor and the therapeutically effective amount of PDE4 inhibitor are administered simultaneously as a combined formulation.

4. The method according to claim 1, wherein the therapeutically effective amount of PI3K Delta or dual PI3K Delta and Gamma inhibitor and the therapeutically effective amount of PDE4 inhibitor are administered sequentially.

5. The method according to claim 4, wherein the therapeutically effective amount of PDE-4 inhibitor is administered before the therapeutically effective amount of PI3K Delta or Dual PI3K Delta and Gamma inhibitor.

6. The method according to claim 1, wherein the therapeutically effective amount of PI3K Delta or dual PI3K Delta and Gamma inhibitor is administered twice daily to once every three weeks, and the therapeutically effective amount of the PDE4 inhibitor is administered twice daily to once every three weeks.

7. The method according to claim 1, wherein the autoimmune, respiratory and/or inflammatory disease or condition is selected from the group consisting of asthma, allergic rhinitis, non-allergic rhinitis, rheumatoid arthritis, chronic obstructive pulmonary disease, and atopic dermatitis.

8. The method according to claim 1, wherein the PI3K Delta or dual PI3K Delta and Gamma inhibitor and at the PDE4 inhibitor are each administered in an amount ranging from about 0.01 mg to about 1000 mg.

9. The method of claim 1, wherein the PI3K Delta or dual PI3K Delta and Gamma inhibitor and the PDE4 inhibitor are administered at a ratio of about 1:100 to about 100:1 by weight.

10. The method of claim 1, wherein the autoimmune, respiratory and/or inflammatory disease or condition is asthma.

11. The method of claim 1, wherein the autoimmune, respiratory and/or inflammatory disease or condition is chronic obstructive pulmonary disease.

12. The method according to claim 1, wherein the PDE-4inhibitor is roflumilast.

13. A pharmaceutical composition comprising (i) a PI3K Delta or dual PI3K Delta and Gamma inhibitor, (ii) a PDE4 inhibitor, and (iii) optionally, a pharmaceutically acceptable carrier, glidant, diluent, or excipient, wherein the PI3K Delta inhibitor is selected from 2-((6-amino-9H-purin-9-yl)methyl)-5-methyl-3-o-tolylquinazolin-4(3H)-one (IC87114) and (S)-2-(1-(9H-purin-6-ylamino)ethyl)-6-fluoro-3-(3-fluorophenyl)-4H-chromen-4-one, and pharmaceutically acceptable salts thereof;

the dual PI3K Delta and Gamma inhibitor is selected from (+)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one, and pharmaceutically acceptable salts thereof; and the PDE4 inhibitor is selected from roflumilast, apremilast, N-(3,5-dichloro-1-oxo -pyridin-4-yl)-4-difluoromethoxy-3-cyclopropylmethoxybenzamide, oglemilastum, D-4418, D-4396(Sch-351591), AWD-12-281 (GW-842470), CDP-840, 2-carbomethoxy-4-cyano-4-(3-cyclopropylmethoxy-4-difluoromethoxy phenyl)cyclohexan- 1-one, cis [4-cyano-4-(3-cyclopropylmethoxy-4-difluoromethoxy phenyl) cyclohexan-1-ol], cilomilast, cis [4-cyano-4-(3-cyclopentyloxy-4-methoxy phenyl) cyclohexan-1-carboxylic acid], (R)-(+)-ethyl[4-(3-cyclopentyloxy-4-methoxyphenyl) pyrrolidin-2-yliden] acetate, (S)-(−)-ethyl[4-(3-cyclopentyloxy-4-methoxyphenyl)pyrrolidin-2-yliden [acetate, CDC-801, CDC-3052, lirimilast (Bay-198004), and pharmaceutically acceptable salts thereof.

14. The pharmaceutical composition according to claim 13, wherein the PDE-4 inhibitor is selected from the group consisting of roflumilast and apremilast, and pharmaceutically acceptable salts.

15. The pharmaceutical composition of claim 13, wherein the composition comprises 0.01 mg to about 1000 mg of the PI3K Delta or Dual PI3K Delta and Gamma inhibitor and 0.01 mg to about 1000 mg of the PDE4 inhibitor.

16. The pharmaceutical composition according to claim 13, wherein the PDE-4 inhibitor is roflumilast.

17. A kit for treating an autoimmune, respiratory or inflammatory disease or condition selected from asthma, chronic obstructive pulmonary disease, rheumatoid arthritis, inflammatory bowel disease, glomerulonephritis, neuroinflammatory diseases, multiple sclerosis, uveitis, psoriasis, arthritis, vasculitis, dermatitis, osteoarthritis, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis, myasthenia gravis, autoimmune hemolytic anemia, cystic fibrosis, chronic relapsing hepatitis, primary biliary cirrhosis, allergic conjunctivitis, atopic dermatitis, and combinations thereof, the kit comprising:
(i) a PI3K Delta or PI3K Delta and Gamma inhibitor, and (ii) a PDE4 inhibitor, either in a single pharmaceutical composition or in separate pharmaceutical compositions,
(ii) optionally, instructions for treating the autoimmune, respiratory or inflammatory disease or condition with the PI3K Delta or PI3K Delta and Gamma inhibitor, and PDE4 inhibitor, and
(iii) optionally, a container for placing the pharmaceutical composition or pharmaceutical compositions, wherein the PI3K Delta inhibitor is selected from 2-((6-amino-9H-purin-9-yl)methyl)-5-methyl-3-o-tolylquinazolin-4 (3H)-one (IC87114), (S)-2-(1-(9H-purin-6-ylamino) ethyl)-6-fluoro-3-(3-fluorophenyl)-4H-chromen-4-one, and pharmaceutically acceptable salts thereof;

the dual PI3K Delta and Gamma inhibitor is selected from (+)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one, and pharmaceutically acceptable salts thereof; and the PDE4 inhibitor is selected from roflumilast, apremilast, N-(3,5-dichloro-1-oxo -pyridin-4-yl)-4-difluoromethoxy-3-cyclopropylmethoxybenzamide, oglemilastum, D-4418, D-4396(Sch-351591), AWD-12-281 (GW-842470), CDP-840, 2-carbomethoxy-4-cyano-4-(3-cyclopropylmethoxy-4-difluoromethoxy phenyl)cyclohexan- 1-one, cis [4-cyano-4-(3-cyclopropylmethoxy-4-difluoromethoxy phenyl) cyclohexan-1-ol], cilomilast, cis [4-cyano-4-(3-cyclopentyloxy-4-methoxy phenyl) cyclohexan-1-carboxylic acid], (R)-(+)-ethyl[4-(3-cyclopentyloxy-4-methoxyphenyl) pyrrolidin-2-yliden] acetate, (S)-(–)-ethyl[4-(3-cyclopentyloxy-4-methoxyphenyl)pyrrolidin-2-yliden [acetate, CDC-801, CDC-3052, lirimilast (Bay-198004), and pharmaceutically acceptable salts thereof.

18. The kit according to claim 17, wherein the PDE-4 inhibitor is roflumilast.

19. A method of treating an autoimmune, respiratory and/or inflammatory disease or condition selected from asthma, chronic obstructive pulmonary disease, rheumatoid arthritis, inflammatory bowel disease, glomerulonephritis, neuroinflammatory diseases, multiple sclerosis, uveitis, psoriasis, arthritis, vasculitis, dermatitis, osteoarthritis, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis, myasthenia gravis, autoimmune hemolytic anemia, cystic fibrosis, chronic relapsing hepatitis, primary biliary cirrhosis, allergic conjunctivitis, atopic dermatitis, and combinations thereof, the method comprising administering to a subject in need thereof a therapeutically effective amount of (i) 2-((6-amino-9H-purin-9-yl)methyl)-5-methyl-3-o-tolylquinazolin-4(3H) -one (IC87114) or a pharmaceutically acceptable salt thereof, and (ii) roflumilast.

20. A method of treating an autoimmune, respiratory and/or inflammatory disease or condition selected from asthma, chronic obstructive pulmonary disease, rheumatoid arthritis, inflammatory bowel disease, glomerulonephritis, neuroinflammatory diseases, multiple sclerosis, uveitis, psoriasis, arthritis, vasculitis, dermatitis, osteoarthritis, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis, myasthenia gravis, autoimmune hemolytic anemia, cystic fibrosis, chronic relapsing hepatitis, primary biliary cirrhosis, allergic conjunctivitis, atopic dermatitis, and combinations thereof, the method comprising administering to a subject in need thereof a therapeutically effective amount of (i) (S)-2-(1-(9H-purin-6-ylamino)ethyl)-6-fluoro-3-(3-fluorophenyl)-4H-chromen-4-one or a pharmaceutically acceptable salt thereof, and (ii) roflumilast.

21. A method of treating an autoimmune, respiratory and/or inflammatory disease or condition selected from asthma, chronic obstructive pulmonary disease, rheumatoid arthritis, inflammatory bowel disease, glomerulonephritis, neuroinflammatory diseases, multiple sclerosis, uveitis, psoriasis, arthritis, vasculitis, dermatitis, osteoarthritis, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis, myasthenia gravis, autoimmune hemolytic anemia, cystic fibrosis, chronic relapsing hepatitis, primary biliary cirrhosis, allergic conjunctivitis, atopic dermatitis, and combinations thereof, the method comprising administering to a subject in need thereof a therapeutically effective amount of (i) (+)-2-(1 -(4-amino-3-(3-fluoro-4-isopropoxyphenyl)-1H-pyrazolo [3,4-d]pyrimidin-1-yl)ethyl)-5-fluoro-3-(3-fluorophenyl)-4H-chromen-4-one or a pharmaceutically acceptable salt thereof, and (ii) roflumilast.

* * * * *